United States Patent
LaVon et al.

(10) Patent No.: US 8,684,990 B2
(45) Date of Patent: Apr. 1, 2014

(54) SIMPLE DISPOSABLE PANT-LIKE GARMENT HAVING BREATHABLE SIDE BARRIERS

(75) Inventors: Gary Dean LaVon, Liberty Township, OH (US); Pankaj Nigam, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 87 days.

(21) Appl. No.: 11/224,462

(22) Filed: Sep. 12, 2005

(65) Prior Publication Data
US 2007/0173782 A1    Jul. 26, 2007

(51) Int. Cl.
| A61F 13/15 | (2006.01) |
| A61F 13/49 | (2006.01) |
| A61F 13/51 | (2006.01) |
| A61F 13/514 | (2006.01) |
| A61F 13/56 | (2006.01) |
| A61F 13/84 | (2006.01) |

(52) U.S. Cl.
USPC .......... 604/396; 604/385.01; 604/385.03; 604/385.04; 604/385.101; 604/385.22; 604/385.24; 604/385.25

(58) Field of Classification Search
USPC ............ 604/389–394, 396, 367, 386, 358.3, 604/385.29, 385.28, 385.27, 385.25, 604/385.23, 385.22, 385.21, 387; 2/400, 2/275; 156/73.1, 66, 308.4, 289, 277, 156/269, 264
See application file for complete search history.

(56) References Cited

U.S. PATENT DOCUMENTS

| 1,733,997 A | 10/1929 | Marr |
| 1,734,499 A | 11/1929 | Marinsky |
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |

(Continued)

FOREIGN PATENT DOCUMENTS

| EP | 0 206 208 A1 | 12/1986 |
| EP | 0 403832A-1 | 12/1990 |

(Continued)

OTHER PUBLICATIONS http://www.bartleby.com/61/43/C0774300.html (dictionary definition of "cruciform," accessed Jun. 18, 2007 ).*

(Continued)

Primary Examiner — Adam Marcetich
(74) Attorney, Agent, or Firm — Richard L. Alexander

(57) ABSTRACT

A simple disposable pant-like garment includes an absorbent assembly attached to a chassis. The absorbent assembly includes an absorbent core that may contain superabsorbent particles, which may be contained inside pockets. The absorbent assembly is folded laterally inward at both of its side edges to form laterally opposing side flaps. Each side flap is attached to an interior surface of the absorbent assembly adjacent to its end edges. A longitudinally extending elastic gathering member is attached to each side flap adjacent to its proximal edge. When the article is worn, the elastic gathering members contract and raise the side flaps to form breathable side barriers. The chassis includes a water-impermeable sheet and may be extensible. The absorbent assembly may be attached in a cruciform pattern such that portions of the chassis that lie outside the attachment pattern are not restrained by attachment to the absorbent assembly and therefore remain extensible.

17 Claims, 12 Drawing Sheets

(56) References Cited

U.S. PATENT DOCUMENTS

| | | |
|---|---|---|
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,207,158 A | 9/1965 | Yoshitake et al. |
| 3,386,442 A | 6/1968 | Sabee |
| 3,561,446 A | 2/1971 | Jones |
| 3,572,342 A | 3/1971 | Lindquist et al. |
| 3,578,155 A | 5/1971 | Small et al. |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 8/1974 | Zoephel |
| 3,840,418 A | 10/1974 | Sabee |
| 3,847,702 A | 11/1974 | Jones |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,074,508 A | 2/1978 | Reid |
| 4,084,592 A | 4/1978 | Tritsch |
| 4,100,922 A | 7/1978 | Hernandez |
| 4,257,418 A | 3/1981 | Hessner |
| 4,296,750 A | 10/1981 | Woon et al. |
| 4,315,508 A | 2/1982 | Bolick |
| 4,324,246 A | 4/1982 | Mullane et al. |
| 4,342,314 A | 8/1982 | Radel et al. |
| 4,388,075 A | 6/1983 | Mesek et al. |
| 4,461,621 A | 7/1984 | Karami et al. |
| 4,463,045 A | 7/1984 | Ahr et al. |
| 4,475,912 A | 10/1984 | Coates |
| 4,490,148 A | 12/1984 | Beckeström |
| 4,585,450 A | 4/1986 | Rosch et al. |
| 4,589,878 A | 5/1986 | Mitrani |
| 4,601,717 A | 7/1986 | Blevins |
| 4,610,678 A | 9/1986 | Weisman et al. |
| 4,636,207 A | 1/1987 | Buell |
| 4,670,011 A | 6/1987 | Mesek |
| 4,680,030 A | 7/1987 | Coates et al. |
| 4,681,581 A | 7/1987 | Coates |
| 4,690,680 A | 9/1987 | Higgins |
| 4,695,278 A * | 9/1987 | Lawson ............... 604/385.27 |
| 4,704,115 A | 11/1987 | Buell |
| 4,704,116 A * | 11/1987 | Enloe ............... 604/385.27 |
| 4,731,066 A | 3/1988 | Korpman et al. |
| 4,747,846 A | 5/1988 | Boland et al. |
| 4,787,896 A | 11/1988 | Houghton et al. |
| 4,795,454 A | 1/1989 | Dragoo |
| 4,802,884 A | 2/1989 | Fröidh et al. |
| 4,808,176 A | 2/1989 | Kielpikowski |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,846,825 A * | 7/1989 | Enloe et al. ............... 604/385.22 |
| 4,861,652 A | 8/1989 | Lippert et al. |
| RE33,106 E * | 11/1989 | Beckestrom ............ 604/385.25 |
| 4,888,231 A | 12/1989 | Angstadt |
| 4,892,528 A | 1/1990 | Suzuki et al. |
| 4,892,536 A | 1/1990 | DesMarais et al. |
| 4,900,384 A * | 2/1990 | Sanders et al. ............... 156/204 |
| 4,904,251 A * | 2/1990 | Igaue et al. ............... 604/385.26 |
| 4,909,802 A | 3/1990 | Ahr et al. |
| 4,909,803 A | 3/1990 | Aziz et al. |
| 4,940,463 A | 7/1990 | Leathers et al. |
| 4,940,464 A | 7/1990 | Van Gompel et al. |
| 4,950,264 A | 8/1990 | Osborn et al. |
| 4,963,140 A | 10/1990 | Robertson et al. |
| 4,968,313 A | 11/1990 | Sabee |
| 4,990,147 A | 2/1991 | Freeland |
| 5,006,394 A | 4/1991 | Baird |
| 5,021,051 A * | 6/1991 | Hiuke ............... 604/385.27 |
| 5,037,416 A | 8/1991 | Allen et al. |
| 5,071,414 A | 12/1991 | Elliott |
| 5,085,654 A | 2/1992 | Buell |
| 5,087,255 A * | 2/1992 | Sims ............... 604/385.23 |
| 5,092,861 A | 3/1992 | Nomura et al. |
| 5,114,420 A | 5/1992 | Igaue et al. |
| 5,135,522 A | 8/1992 | Fahrenkrug et al. |
| D329,697 S | 9/1992 | Fahrenkrug et al. |
| 5,151,092 A | 9/1992 | Buell et al. |
| 5,190,606 A | 3/1993 | Merkatoris et al. |
| 5,204,997 A | 4/1993 | Suzuki et al. |
| 5,221,274 A | 6/1993 | Buell et al. |
| 5,235,515 A | 8/1993 | Ungpiyakul et al. |
| 5,246,431 A | 9/1993 | Minetola et al. |
| 5,246,432 A | 9/1993 | Suzuki et al. |
| 5,246,433 A | 9/1993 | Hasse et al. |
| 5,260,345 A | 11/1993 | Desmarais et al. |
| 5,269,775 A | 12/1993 | Freeland et al. |
| 5,312,386 A | 5/1994 | Correa et al. |
| 5,358,500 A | 10/1994 | LaVon et al. |
| 5,366,782 A | 11/1994 | Curro et al. |
| 5,387,209 A | 2/1995 | Yamamoto et al. |
| 5,397,316 A | 3/1995 | Lavon et al. |
| H1440 H | 5/1995 | New et al. |
| 5,454,803 A * | 10/1995 | Sageser et al. ............ 604/385.28 |
| 5,476,458 A | 12/1995 | Glaug et al. |
| 5,518,801 A | 5/1996 | Chappell et al. |
| 5,531,730 A | 7/1996 | Dreier |
| 5,549,592 A | 8/1996 | Fries et al. |
| 5,549,593 A | 8/1996 | Ygge et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,584,829 A | 12/1996 | Lavash et al. |
| 5,599,417 A * | 2/1997 | Glaug et al. ............... 156/227 |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |
| 5,622,589 A | 4/1997 | Johnson et al. |
| 5,624,424 A * | 4/1997 | Saisaka et al. ............ 604/385.28 |
| 5,625,222 A | 4/1997 | Yoneda et al. |
| 5,626,571 A | 5/1997 | Young et al. |

| | | | |
|---|---|---|---|
| 5,635,191 A | 6/1997 | Roe et al. | |
| 5,643,243 A | 7/1997 | Klemp | |
| 5,643,588 A | 7/1997 | Roe et al. | |
| H1674 H | 8/1997 | Ames et al. | |
| 5,662,638 A | 9/1997 | Johnson et al. | |
| 5,674,215 A | 10/1997 | Ronnberg | |
| 5,685,874 A * | 11/1997 | Buell et al. | 604/396 |
| 5,691,035 A | 11/1997 | Chappell et al. | |
| 5,723,087 A | 3/1998 | Chappell et al. | |
| 5,749,866 A | 5/1998 | Roe et al. | |
| 5,752,947 A | 5/1998 | Awolin | |
| 5,772,825 A | 6/1998 | Schmitz | |
| 5,776,121 A * | 7/1998 | Roe et al. | 604/385.25 |
| 5,779,831 A | 7/1998 | Schmitz | |
| 5,797,894 A | 8/1998 | Cadieux et al. | |
| 5,810,800 A | 9/1998 | Hunter et al. | |
| 5,814,035 A | 9/1998 | Gryskiewicz et al. | |
| 5,846,232 A | 12/1998 | Serbiak et al. | |
| 5,851,204 A | 12/1998 | Mizutani | |
| 5,865,823 A | 2/1999 | Curro | |
| 5,873,868 A | 2/1999 | Nakahata et al. | |
| 5,876,391 A | 3/1999 | Roe et al. | |
| 5,891,544 A | 4/1999 | Chappell et al. | |
| 5,897,545 A | 4/1999 | Kline et al. | |
| 5,904,673 A | 5/1999 | Roe et al. | |
| 5,919,179 A * | 7/1999 | Faulks et al. | 604/385.23 |
| 5,931,825 A | 8/1999 | Kuen et al. | |
| 5,951,536 A | 9/1999 | Osborn, III et al. | |
| 5,957,908 A | 9/1999 | Kline et al. | |
| 5,968,029 A | 10/1999 | Chappell et al. | |
| 5,997,521 A * | 12/1999 | Robles et al. | 604/385.22 |
| 6,004,306 A | 12/1999 | Robles et al. | |
| 6,022,430 A | 2/2000 | Blenke et al. | |
| 6,022,431 A | 2/2000 | Blenke et al. | |
| 6,042,673 A | 3/2000 | Johnson et al. | |
| 6,102,892 A | 8/2000 | Putzer et al. | |
| 6,107,537 A | 8/2000 | Elder et al. | |
| 6,110,157 A | 8/2000 | Schmidt | |
| 6,120,486 A | 9/2000 | Toyoda et al. | |
| 6,120,487 A | 9/2000 | Ashton | |
| 6,120,489 A | 9/2000 | Johnson | |
| 6,120,866 A | 9/2000 | Arakawa et al. | |
| 6,129,720 A | 10/2000 | Blenke et al. | |
| 6,156,023 A * | 12/2000 | Yoshioka | 604/385.29 |
| 6,156,424 A | 12/2000 | Taylor | |
| 6,165,160 A | 12/2000 | Suzuki et al. | |
| 6,174,302 B1 | 1/2001 | Kumasaka | |
| 6,177,607 B1 | 1/2001 | Blaney et al. | |
| 6,186,996 B1 | 2/2001 | Martin | |
| 6,210,390 B1 | 4/2001 | Karlsson | |
| 6,238,380 B1 | 5/2001 | Sasaki | |
| 6,241,716 B1 | 6/2001 | Rönnberg | |
| 6,322,552 B1 * | 11/2001 | Blenke et al. | 604/540 |
| 6,325,787 B1 | 12/2001 | Roe et al. | |
| 6,334,858 B1 | 1/2002 | Rönnberg et al. | |
| 6,350,332 B1 | 2/2002 | Thomas et al. | |
| 6,402,729 B1 | 6/2002 | Boberg et al. | |
| 6,402,731 B1 | 6/2002 | Suprise et al. | |
| 6,410,820 B1 | 6/2002 | McFall et al. | |
| 6,413,249 B1 | 7/2002 | Turi et al. | |
| 6,419,667 B1 | 7/2002 | Avalon et al. | |
| 6,423,048 B1 * | 7/2002 | Suzuki et al. | 604/385.28 |
| 6,432,098 B1 | 8/2002 | Kline et al. | |
| 6,432,099 B2 | 8/2002 | Rönnberg | |
| 6,443,933 B1 * | 9/2002 | Suzuki et al. | 604/385.04 |
| 6,461,342 B2 | 10/2002 | Tanji et al. | |
| 6,461,343 B1 | 10/2002 | Schaefer et al. | |
| 6,464,677 B1 * | 10/2002 | Noguchi et al. | 604/385.27 |
| 6,475,201 B2 | 11/2002 | Saito et al. | |
| 6,494,872 B1 | 12/2002 | Suzuki et al. | |
| 6,494,873 B2 | 12/2002 | Karlsson et al. | |
| 6,520,947 B1 | 2/2003 | Tilly et al. | |
| 6,524,294 B1 | 2/2003 | Hilston et al. | |
| 6,579,275 B1 * | 6/2003 | Pozniak et al. | 604/390 |
| 6,585,713 B1 | 7/2003 | LaMahieu et al. | |
| 6,602,234 B2 | 8/2003 | Klemp et al. | |
| 6,605,070 B2 | 8/2003 | Ludwig et al. | |
| 6,648,869 B1 | 11/2003 | Gillies et al. | |
| 6,648,870 B2 | 11/2003 | Itoh et al. | |
| 6,648,871 B2 | 11/2003 | Kusibojoska et al. | |
| 6,682,515 B1 | 1/2004 | Mizutani et al. | |
| 6,689,115 B1 | 2/2004 | Popp et al. | |
| 6,692,476 B1 * | 2/2004 | Minato et al. | 604/385.27 |
| 6,716,205 B2 * | 4/2004 | Popp et al. | 604/385.24 |
| 6,726,792 B1 | 4/2004 | Johnson et al. | |
| 6,818,083 B2 | 11/2004 | Mcamish et al. | |
| 6,880,211 B2 | 4/2005 | Jackson et al. | |
| 6,923,797 B2 | 8/2005 | Shinohara et al. | |
| 6,962,578 B1 | 11/2005 | LaVon | |
| 6,972,010 B2 | 12/2005 | Pesce et al. | |
| 7,014,632 B2 | 3/2006 | Takino et al. | |
| 7,037,299 B2 | 5/2006 | Turi et al. | |
| 7,048,726 B2 | 5/2006 | Kusagawa et al. | |
| 7,160,281 B2 | 1/2007 | Leminh et al. | |
| 2001/0016723 A1 * | 8/2001 | Sayama et al. | 604/398 |
| 2001/0039408 A1 * | 11/2001 | Tanji et al. | 604/385.26 |
| 2002/0045881 A1 | 4/2002 | Kusibojoska et al. | |
| 2002/0058923 A1 * | 5/2002 | Suprise et al. | 604/391 |
| 2002/0087139 A1 | 7/2002 | Popp et al. | |
| 2002/0151861 A1 | 10/2002 | Klemp et al. | |
| 2002/0165515 A1 * | 11/2002 | Burnham | 604/385.14 |
| 2002/0173764 A1 * | 11/2002 | Takino et al. | 604/385.28 |
| 2002/0173767 A1 | 11/2002 | Popp et al. | |
| 2003/0009143 A1 | 1/2003 | Ludwig et al. | |
| 2003/0088223 A1 | 5/2003 | Vogt et al. | |
| 2003/0088230 A1 | 5/2003 | Balogh et al. | |
| 2003/0093056 A1 * | 5/2003 | Kurata | 604/385.101 |
| 2003/0120248 A1 | 6/2003 | Miyamoto | 604/385.28 |
| 2003/0144644 A1 | 7/2003 | Murai et al. | |
| 2003/0148694 A1 | 8/2003 | Ghiam | |
| 2003/0167046 A1 * | 9/2003 | Klemp et al. | 604/383 |
| 2003/0233082 A1 | 12/2003 | Kline et al. | |
| 2004/0022998 A1 | 2/2004 | Miyamoto et al. | |
| 2004/0024379 A1 * | 2/2004 | LaVon et al. | 604/394 |
| 2004/0082928 A1 | 4/2004 | Pesce et al. | |
| 2004/0122411 A1 | 6/2004 | Hancock-Cooke | |
| 2004/0147891 A1 * | 7/2004 | Sugito et al. | 604/385.01 |
| 2004/0158224 A1 * | 8/2004 | Kline et al. | 604/385.31 |
| 2004/0162536 A1 * | 8/2004 | Becker et al. | 604/367 |
| 2004/0167486 A1 * | 8/2004 | Busam et al. | 604/367 |
| 2004/0225271 A1 | 11/2004 | Datta et al. | |
| 2004/0236299 A1 | 11/2004 | Tsang et al. | |
| 2004/0249355 A1 | 12/2004 | Tanio et al. | |
| 2004/0260264 A1 * | 12/2004 | Otsubo | 604/396 |
| 2005/0004548 A1 | 1/2005 | Otsubo et al. | |
| 2005/0010184 A1 * | 1/2005 | Klemp et al. | 604/385.01 |
| 2005/0038401 A1 | 2/2005 | Suzuki et al. | |
| 2005/0038404 A1 * | 2/2005 | Takino et al. | 604/385.27 |
| 2005/0085784 A1 | 4/2005 | LeMinh et al. | |
| 2005/0171499 A1 | 8/2005 | Nigam et al. | |
| 2005/0203475 A1 | 9/2005 | LaVon et al. | |
| 2005/0267436 A1 * | 12/2005 | Mishima et al. | 604/385.19 |
| 2005/0288645 A1 | 12/2005 | LaVon | |
| 2005/0288646 A1 | 12/2005 | LaVon | |
| 2005/0288648 A1 * | 12/2005 | Otsubo et al. | 604/385.201 |
| 2006/0009746 A1 * | 1/2006 | Nakajima et al. | 604/385.19 |
| 2006/0184151 A1 * | 8/2006 | Onishi et al. | 604/385.19 |
| 2006/0264860 A1 | 11/2006 | Beck | |

FOREIGN PATENT DOCUMENTS

| | | |
|---|---|---|
| EP | 0 761 194 A2 | 3/1997 |
| EP | 0 893 115 A2 | 1/1999 |
| EP | 0 951 890 A2 | 1/1999 |
| EP | 0904756 A | 3/1999 |
| EP | 0916327 A1 | 5/1999 |
| EP | 0 793 469 B1 | 6/2002 |
| EP | 1 224 922 A2 | 7/2002 |
| EP | 1273281 A | 1/2003 |
| EP | 0 951 886 B1 | 7/2004 |
| EP | 1 447 066 A1 | 8/2004 |
| EP | 1 447 067 A1 | 8/2004 |
| ES | 2 213 491 A1 | 8/2004 |
| FR | 2 566 631 A1 | 1/1986 |
| FR | 2 612 770 A1 | 9/1988 |
| FR | 2 810 234 A1 | 12/2001 |
| GB | 1 513 055 | 6/1978 |

(56) References Cited

FOREIGN PATENT DOCUMENTS

| GB | 2 101 468 A | 1/1983 |
|---|---|---|
| GB | 2 262 873 A | 7/1993 |
| JP | 04 122256 A | 4/1992 |
| JP | 11318980 | 11/1999 |
| WO | WO7900008 A1 | 1/1979 |
| WO | WO8800441 A1 | 1/1988 |
| WO | WO9516746 A1 | 6/1995 |
| WO | WO95/19753 A | 7/1995 |
| WO | WO 95/29657 A1 | 11/1995 |
| WO | WO9725891 A1 | 7/1997 |
| WO | WO9733547 A1 | 9/1997 |
| WO | WO 98/16179 A1 | 4/1998 |
| WO | WO9829081 A | 7/1998 |
| WO | WO9837847 A1 | 9/1998 |
| WO | WO 99/13813 A1 | 9/1999 |
| WO | WO0023020A-1 | 4/2000 |
| WO | WO03/003961 A | 1/2003 |
| WO | WO 03/009794 A2 | 2/2003 |
| WO | WO2004/103234 A | 12/2004 |
| WO | WO 2004/105664 | 12/2004 |
| WO | WO/2005/060910 A | 7/2005 |
| WO | WO 2005/087164 A1 | 9/2005 |
| WO | WO 2007/000315 A1 | 1/2007 |

OTHER PUBLICATIONS http://www.bartleby.com/61/36/C0773600.html (dictionary definition of "cruciate," accessed Jun. 18, 2007).*
U.S. Appl. No. 10/776,839, filed Feb. 12, 2003, Busam et al.
U.S. Appl. No. 10/776,851, filed Feb. 12, 2003, Becker et al.
The International Search Report PCT/IB2006/053239 mailed Feb. 27, 2007.

* cited by examiner

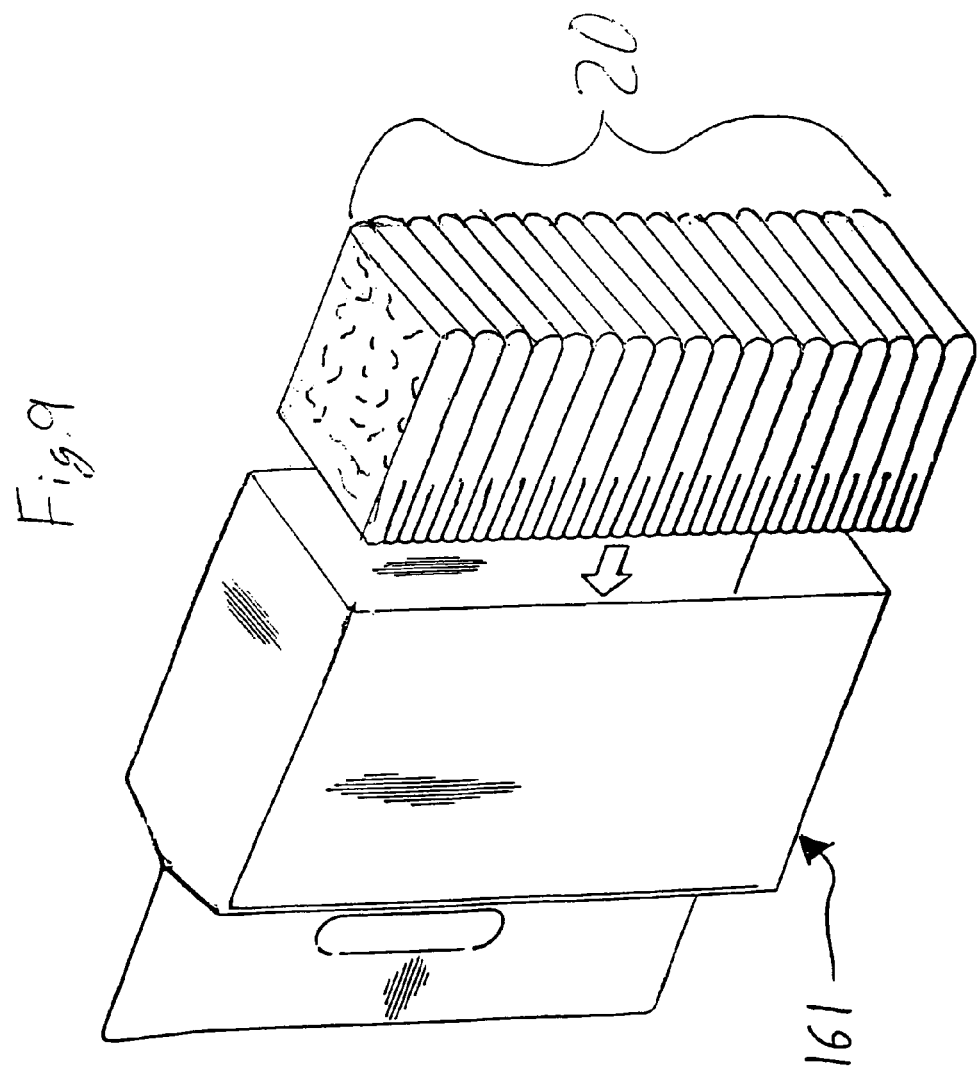

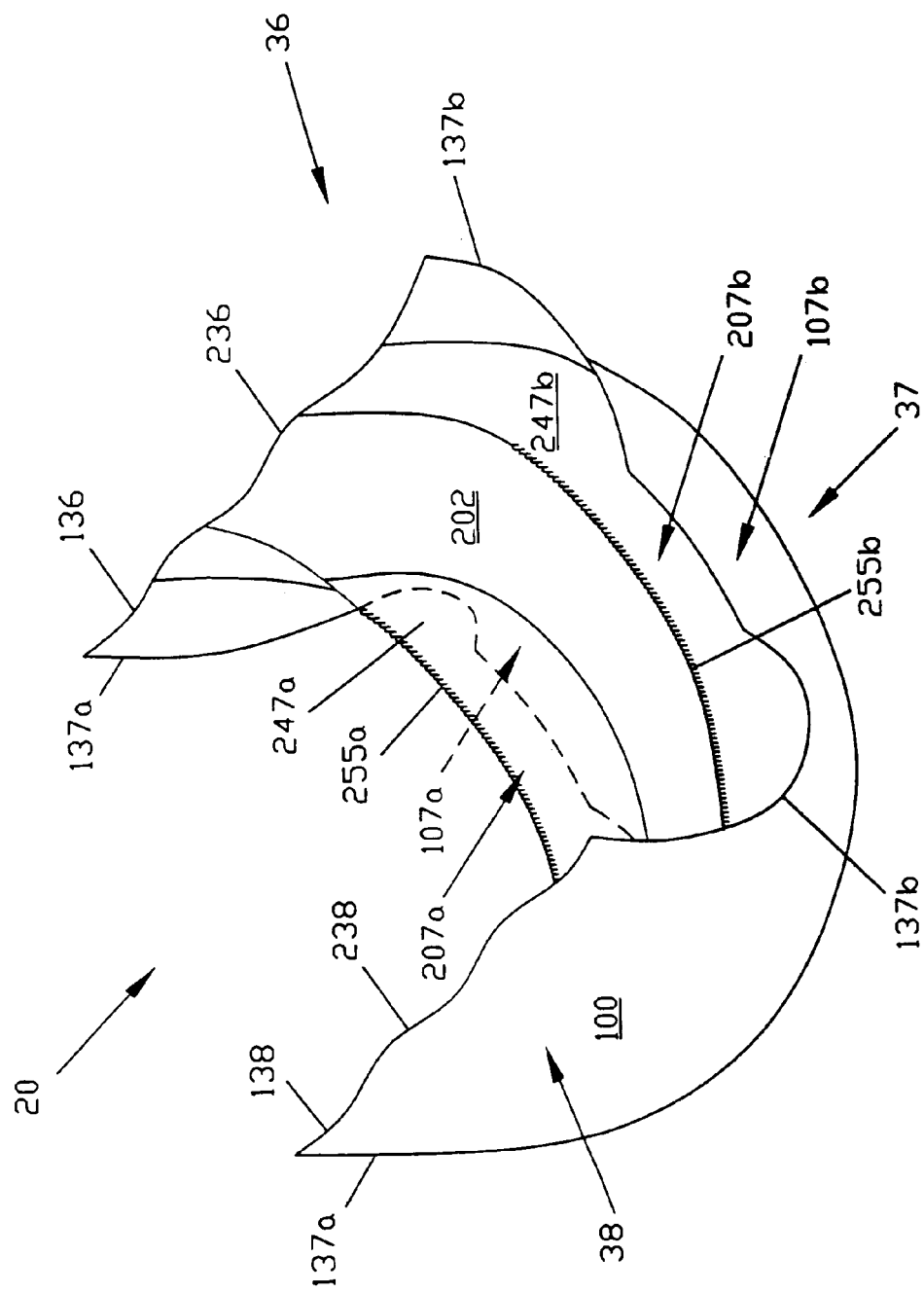

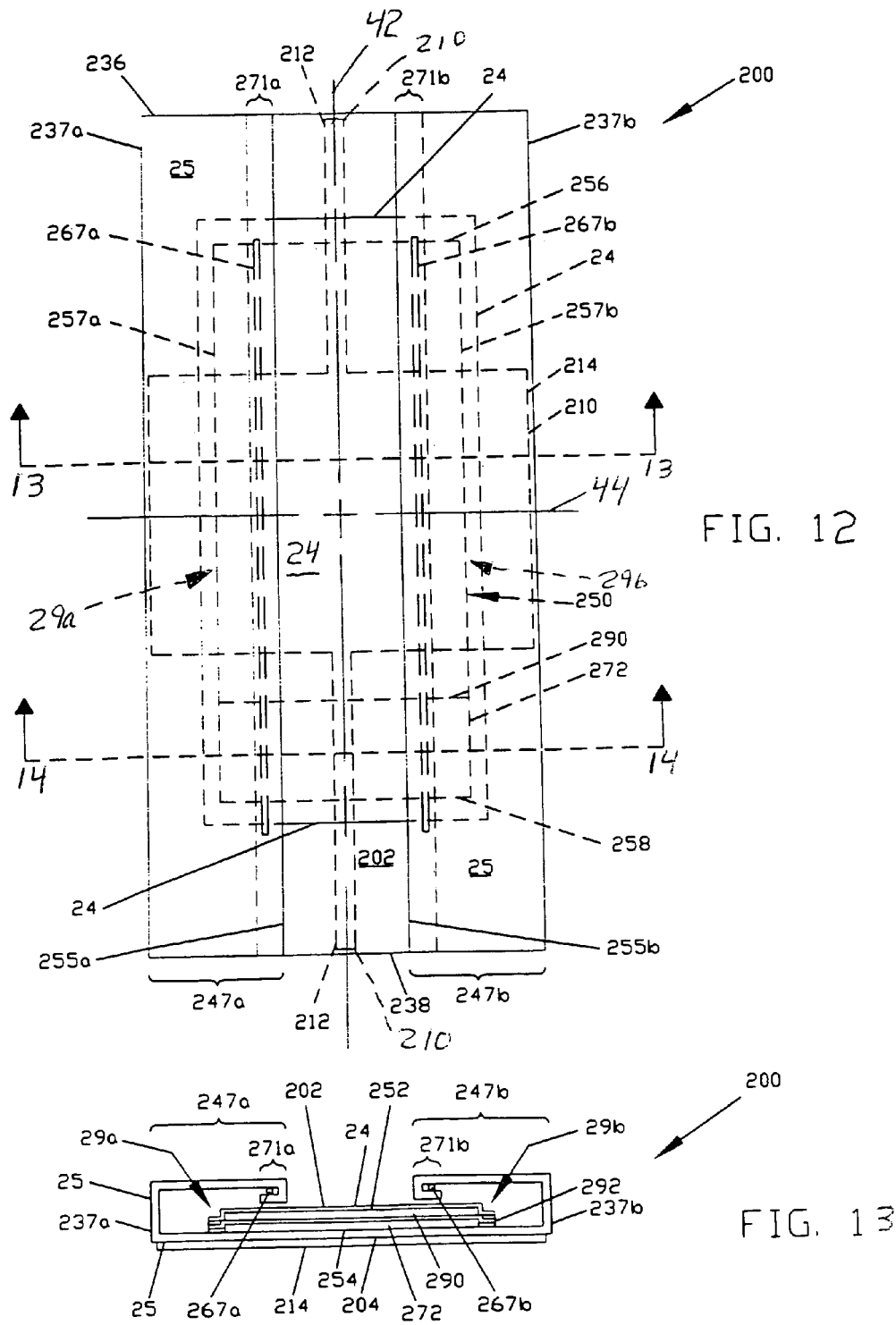

SIMPLE DISPOSABLE PANT-LIKE GARMENT HAVING BREATHABLE SIDE BARRIERS

FIELD OF THE INVENTION

This invention relates to disposable absorbent articles such as disposable diapers and other articles intended for use on incontinent persons, and in particular relates to such absorbent articles configured as pant-like garments.

BACKGROUND OF THE INVENTION

Disposable absorbent articles are designed to absorb and contain bodily waste in order to prevent soiling of the body and clothing of the wearer, as well as bedding or other objects with which the wearer comes into contact. Pant-like garments, especially those of the "pull-on" type, include a pair of closed side interfaces that define encircled waist and leg openings. Accordingly, pull-on diapers can be more easily applied especially to a standing wearer than taped diapers, which require manual fastening to secure the diaper on the wearer.

As the usage of disposable absorbent articles has expanded, their complexity has increased with the incorporation of additional features serving to enhance their performance and appearance. While such features have proven suitable for their intended purpose, the costs of the materials and the costs of the manufacturing processes of complex articles have increased to the point where the prices at which these articles are sold have risen to levels that many potential purchasers around the world cannot afford to pay.

One such additional feature incorporated into conventional disposable absorbent articles is a barrier leg cuff. Typically a pair of spaced barrier leg cuffs is oriented along the opposing longitudinal outer edges of a given absorbent article at the crotch region. The barrier leg cuffs extend, typically under a force provided by an elastic member, toward the wearer's body to provide side barrier protection that reduces or prevents leakage. Barrier leg cuffs are typically incorporated into conventional absorbent articles by attaching discrete leg cuff members to an existing chassis. Unfortunately, the costs to fabricate and install discrete members increases the overall manufacture costs of the absorbent articles, thereby increasing the costs to purchase such absorbent articles at the point of sale.

What is therefore needed is a simple absorbent article providing side barrier protection that can be manufactured more efficiently than conventional absorbent articles that include discrete barrier leg cuff members.

SUMMARY OF THE INVENTION

The present invention provides a disposable pant-like garment having breathable side barriers.

In accordance with one aspect of the present invention, a disposable pant-like garment is provided having a front waist region, a back waist region, and a crotch region between the waist regions. The garment includes an absorbent assembly and a chassis. The absorbent assembly has an interior surface and an exterior surface and laterally opposing longitudinally extending breathable side flaps. Each side flap has longitudinally opposing ends and a longitudinally extending proximal edge. Each side flap is attached adjacent to its ends to the interior surface of the absorbent assembly. Each side flap has a longitudinally extending elastic gathering member attached adjacent to its proximal edge such that, when allowed to relax, the elastic gathering member contracts and lifts the proximal edge away from the interior surface of the absorbent assembly, thereby raising the side flap to form a breathable side barrier. The chassis is attached to the exterior surface of the absorbent assembly. The chassis includes a water-impermeable backsheet. At least a portion of the chassis is extensible. The chassis is pre-closed and configured to encircle the waist and legs of a wearer prior to donning the garment onto the wearer.

In accordance with another aspect of the present invention, a disposable pant-like garment is provided having a front waist region, a back waist region, and a crotch region between the waist regions. The disposable pant-like garment includes an absorbent assembly and a chassis. The absorbent assembly has first and second opposing surfaces and laterally opposing longitudinally extending breathable side flaps. Each side flap has longitudinally opposing ends attached to the first surface of the absorbent assembly. Each side flap further has a longitudinally extending proximal edge. The absorbent assembly further includes a longitudinally extending elastic gathering member attached adjacent to the proximal edge of each side flap such that the elastic gathering member is configured to contract and lift the proximal edge away from the first surface of the absorbent assembly, thereby raising the side flap to form a breathable side barrier. The chassis is attached to the second surface of the absorbent assembly and includes a water-impermeable backsheet.

BRIEF DESCRIPTION OF THE DRAWINGS

In the accompanying drawing figures, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

FIG. 9 is a schematic view of a plurality of prepackaged pull-on diapers constructed in accordance with the present invention;

FIG. 11 is a perspective view of an exemplary diaper, with the interior portion of the diaper that faces inwardly toward the wearer and contacts the wearer shown facing the viewer, in which the diaper is shown in its relaxed, contracted state (i.e., with the contraction induced by elastic members);

FIG. 12 is a plan view of an exemplary absorbent assembly, with the interior portion of the absorbent assembly that faces inwardly toward the wearer and contacts the wearer is shown facing the viewer, in which the absorbent assembly is shown separately from a chassis to which it is attached in an exemplary diaper;

FIG. 13 is a section view of the absorbent assembly illustrated in FIG. 12 taken along line 13-13;

DETAILED DESCRIPTION OF THE INVENTION

Figure 1:
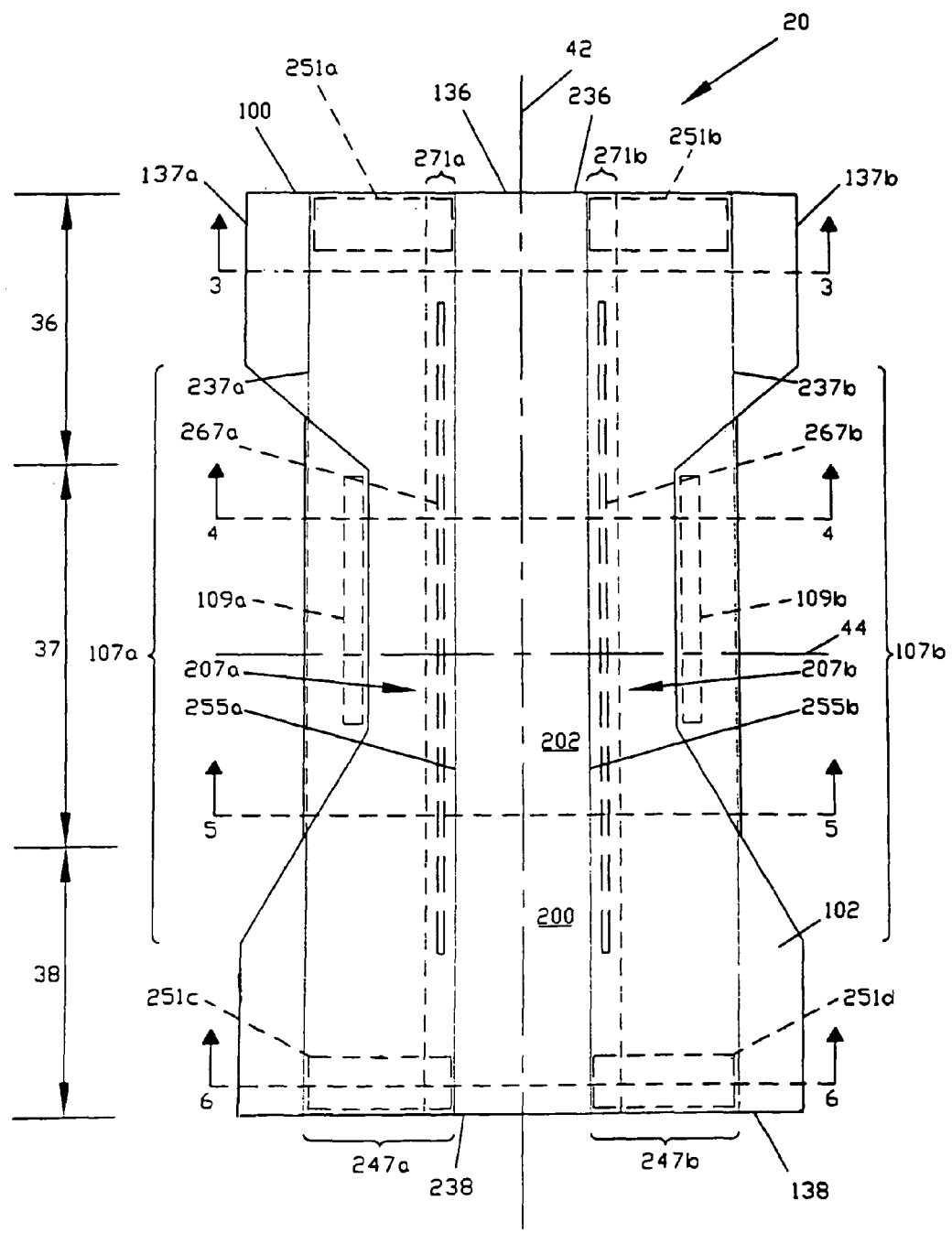
FIG. 1 is a plan view of a disposable absorbent article prior to being configured as a pull-on diaper with the interior portion of the diaper that faces inwardly toward the wearer and contacts the wearer shown facing the viewer, in which the diaper is shown in its flat, uncontracted state (i.e., without the contraction induced by elastic members)
Figure 2:
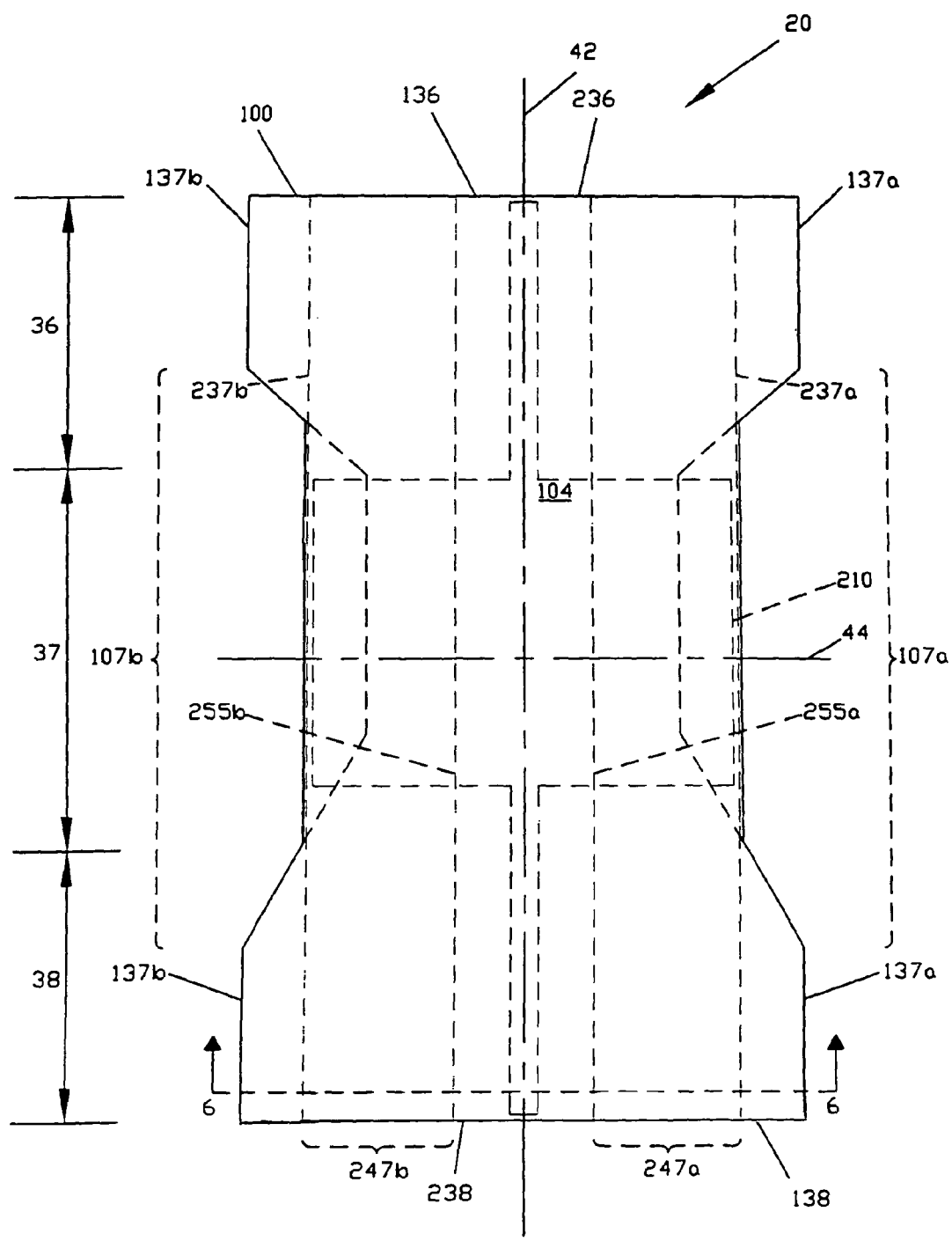
FIG. 2 is a plan view of the absorbent article illustrated in FIG. 1 in its flat, uncontracted state, with the exterior portion of the diaper that faces outwardly away from the wearer shown facing the viewer.
Figure 3:
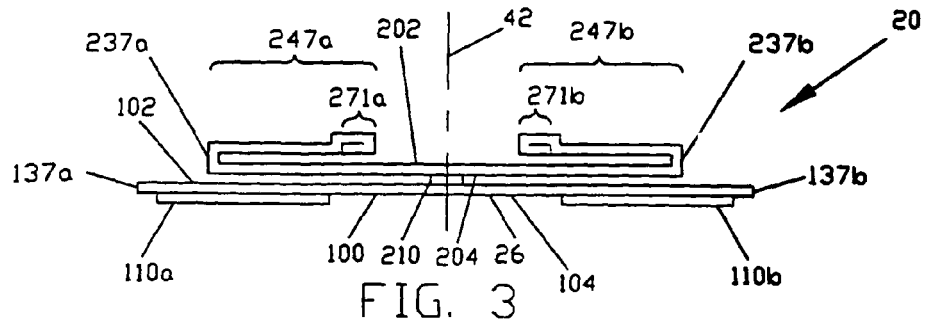
FIG. 3 is a sectional side elevation view of the diaper illustrated in FIG. 1 taken along line 3-3.

In this description, the following terms have the following meanings:

The term "absorbent article" refers to a device that absorbs and contains liquid, and more specifically, refers to a device that is placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

The term "diaper" refers to an absorbent article that is generally worn by infants and incontinent persons about the lower torso so as to encircle the waist and the legs of the wearer and that is specifically adapted to receive and contain urinary and fecal waste.

The term "closed side interface" refers to a given side edge (or a region adjacent the side edge), wherein a portion of the side edge (or a region adjacent the side edge) in the front waist region is joined to a portion of the same side edge (or a region adjacent the side edge) in the rear waist region to define closed, encircled leg openings and a closed waist opening. The side interface can be closed with a refastenable or permanent closure member.

The term "pant" (also referred to as "training pant", "closed diaper", "pull-on diaper", and "pant-like garment") refers to disposable garments having a continuous perimeter waist opening and continuous perimeter leg openings designed for infant or adult wearers. A pant can be configured with a continuous or closed waist opening and at least one continuous, closed, leg opening prior to the article being applied the wearer for use. A pant can be preformed by any suitable technique including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened, front waist fastened, rear waist fastened). Examples of suitable pants are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082 A1.

The term "closure member" refers to an element that maintains the article waist and leg openings in a closed, continuous, configuration until the closure member is released. Suitable closure members include a seam, an adhesive, a cohesive, a heat bond, a pressure bond or weld, a tab-and-slot configuration, a hook-and-loop configuration, and the like.

The term "refastenable closure member" refers to a closure member that can be opened and subsequently re-closed, reliably, without destroying the closure member or surrounding diaper components. Examples of refastenable closure members include peelable adhesives, cohesives, and the like, and mechanical fasteners such as tabs-and-slots, hooks-and-loops, and the like.

The term "permanent closure member" refers to a closure member that can only be destructively opened (i.e., cannot be opened without causing the closure member to fail). Accordingly, a permanent closure member cannot be opened and subsequently reliably closed. At times, when attempting to open a permanent closure member, surrounding absorbent article component(s) may be damaged or torn. Examples of permanent closure members include adhesives, cohesives, and the like, as well as seams.

The term "seam" refers to an elongated line of junction that attaches two regions of a diaper chassis. Seams can be created from permanent thermal bonds, pressure bonds, ultrasonic bonds, permanent adhesive bonds, permanent cohesive bonds, welds, and stitching.

The term "cohesive" refers to the property of a material that sticks to itself but does not to any significant degree stick to other materials.

The term "disposable" refers to the nature of absorbent articles that generally are not intended to be laundered or otherwise restored or reused as an absorbent article, i.e., they are intended to be discarded after a single use and, preferably, to be recycled, composted or otherwise disposed of in an environmentally compatible manner.

The term "extensible" refers to any material which, upon application of a biasing force of less than 500 grams/inch is elongatable, at least about 20 percent without experiencing catastrophic failure.

The term "longitudinal" refers to a direction running from a waist edge to an opposing waist edge of the article and generally parallel to the maximum linear dimension of the article. Directions within ±45° of the longitudinal direction are considered to be "longitudinal".

The term "lateral" refers to a direction running from a side edge to an opposing side edge of the article and generally at a right angle to the longitudinal direction. Directions within ±45° of the lateral direction are considered to be "lateral".

The term "disposed" refers to an element or region being attached and positioned in a particular place or position in a unitary structure with other elements.

The term "attached" refers to elements being connected or united by fastening, adhering, bonding, and the like (i.e., by any method suitable for the elements being attached together and their constituent materials). Many suitable methods for attaching elements together are well-known, including adhesive bonding, pressure bonding, thermal bonding, mechanical fastening, and the like. Such attachment methods can be used to attach elements together over a particular area either continuously or intermittently.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition can be permeable to water vapor, i.e., can be "water vapor-permeable". Such a water vapor-permeable layer or layered structure is commonly known in the art as "breathable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The terms "proximal" and "distal" refer respectively to the location of an element relatively near to or far from the center of a structure, e.g., the proximal edge of a longitudinally extending element is located nearer to the longitudinal axis than the distal edge of the same element is located relative to the same longitudinal axis.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower" and "top" and "bottom", respectively.

Description of Exemplary Diaper Embodiments

As shown in FIGS. 1-6, one longitudinal end portion of an absorbent article, illustrated as an exemplary pant-like garment, also referred to as a pant or a pull-on diaper 20, is configured as a front waist region 36, while the longitudinally opposing end portion is configured as a back waist region 38, and an intermediate portion is configured as a crotch region 37.

The basic structure of the diaper 20 includes a chassis 100, which has a laterally extending front waist edge 136 disposed in the front waist region 36, and a longitudinally opposing and laterally extending back waist edge 138 disposed in the back waist region 38. The chassis 100 has a longitudinally extending left side edge 137a, and a laterally opposing and longitudinally extending right side edge 137b, both chassis side edges extending longitudinally between the front waist edge 136 and the back waist edge 138. The chassis has an interior surface 102, and an exterior surface 104. The chassis 100 defines a longitudinal axis 42 and a lateral axis 44. The longitudinal axis 42 extends through the midpoints of the front waist edge 136 and the back waist edge 138 and a lateral axis 44 extends through the midpoints of the left side edge 137a and the right side edge 137b.

The basic structure of the pull-on diaper 20 also includes an absorbent assembly 200 that is attached to the chassis 100. The absorbent assembly 200 has a laterally extending front edge 236 disposed in the front waist region 36, and a longitudinally opposing and laterally extending back edge 238 disposed in the back waist region 38. The absorbent assembly 200 has a longitudinally extending left side edge 237a, and a laterally opposing and longitudinally extending right side edge 237b, both absorbent assembly side edges extending longitudinally between the front edge 236 and the back edge 238. The absorbent assembly 200 has an interior surface 202 and an exterior surface 204. The absorbent assembly 200 can be disposed symmetrically or asymmetrically with respect to either or both of the longitudinal axis 42 and the lateral axis 44. As illustrated in FIG. 1, the absorbent assembly 200 is symmetrical with respect to both the longitudinal axis 42 and the lateral axis 44. The absorbent assembly 200 has laterally opposing side flaps 247a and 247b that are described in more detail below.

As shown in FIGS. 8A-8D, when the pull-on diaper 20 is worn on the lower torso of a wearer, the front waist edge 136 and the back waist edge 138 encircle the waist of the wearer while, at the same time, the chassis side edges 137a and 137b encircle the legs of the wearer, and thus define left and right leg openings 125a and 125b, respectively. The crotch region 37 is generally positioned between the legs of the wearer, such that the absorbent assembly 200 extends from the front waist region 36 through the crotch region 37 to the back waist region 38.

Figure 8A:
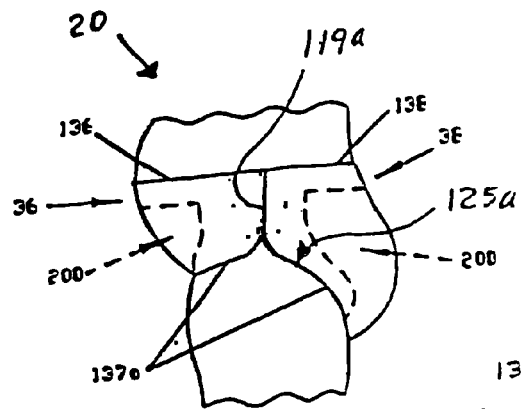
FIG. 8A is a simplified left side elevation view of an exemplary pull-on diaper showing the diaper worn about a lower torso region of a wearer.
Figure 8B:
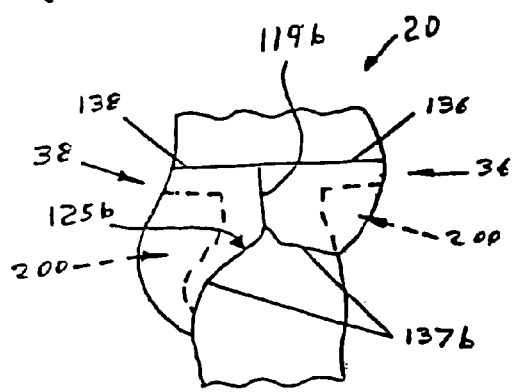
FIG. 8B is a simplified right side elevation view of the pull-on diaper illustrated in FIG. 8A showing the diaper worn about the lower torso region of the wearer.
Figure 8C:
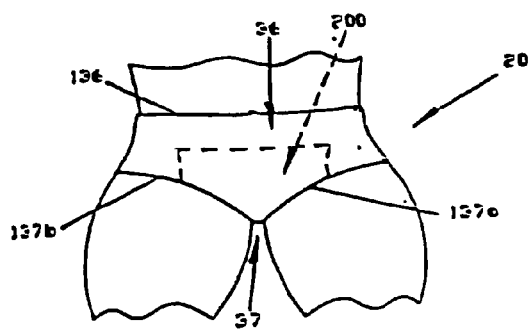
FIG. 8C is a front elevation view of the diaper illustrated in FIGS. 8A-B being worn about the lower torso region of the wearer.
Figure 8D:
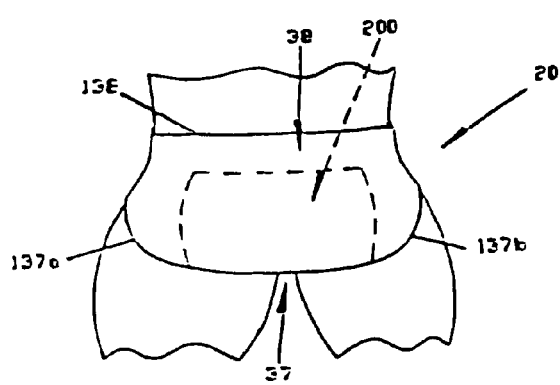
FIG. 8D is a back elevation view of the diaper illustrated in FIGS. 8A-B being worn about the lower torso region of the wearer.

Furthermore, as illustrated in FIGS. 1 and 8A-B, a garment can be preformed by the manufacturer to create a pull-on diaper or pant 20. Specifically, the diaper 20 includes left and right closed side interfaces 119a and 119b, each disposed at left and right side edge regions 145a and 145b, respectively, which are defined as regions adjacent, and including, the respective side edge 137a and 137b and being disposed in the waist regions 36 and 38. The side edge regions 145a and 145b can extend as longitudinally inward from front and back waist edges 136 and 138 as desired. Moreover, the side edge regions 145a and 145b can terminate longitudinally inward from front and back side edges 136 and 138. The closed left side interface 119a is defined by an attachment between 1) the left side edge region 145a at a front left attachment zone 143a disposed in the front waist region 36, and 2) the left side edge region 145a at a back left attachment zone 150a disposed in the back waist region 38. Similarly, the closed right side interface 119b is defined by an attachment between 1) the right side edge region 145b at a front right attachment zone 143b disposed in the front waist region 36, and 2) the right side edge region 145b at a back attachment zone 150b disposed in the back waist region 38. The attachment zones 143a-b may or may not extend to the corresponding waist edges 136 and 138, and may or may not extend to the corresponding side edges 137a and 137b. Furthermore, one skilled in the art will appreciate that the attachment zones 143a-b could be closed using any permanent or refastenable closure member. The attachment zones 143a-b at the side edge regions 145a-b can be attached to form closed side interfaces 119a-b by buttressing and subsequently attaching the side edge 137a in the front and back waist regions 36 and 38, and side edge 137b in the front and back waist regions, respectively, either using a permanent or refastenable closure member, as illustrated in FIGS. 8A-B.

Because the diaper 20 is configured as a pull-on diaper, both side interfaces 119a and 119b are pre-closed, meaning that the side interfaces 119a-b are closed prior to removal of the diaper 20 from its package 161, as illustrated in FIG. 9, and therefore prior to being donned on the wearer. The closed side interfaces 119a-b, in part, define the continuous, closed, left and right leg openings 125a and 125b, respectively, and a continuous, closed, waist opening 144, adapted to fit and gasket the wearer's legs and waist, respectively, as the diaper 20 is pulled up to the wearer's lower torso region. The side interfaces 119a-b can be formed into a closed configuration in accordance with any known techniques or methods known in the art. For instance, the interfaces 119a and 119b can be formed with a permanent seam, which can include a bond formed by heat sealing such as ultrasonic bonding, high pressure bonding, RF (radio frequency) bonding, hot air bonding, heated point bonding, and the like as appreciated by one having ordinary skill in the art. Various suitable pant configurations are disclosed in U.S. Pat. No. 5,246,433 (issued on Sep. 21, 1993 to Margeret H. Hasse, et al); U.S. Pat. No. 5,569,234 (issued on Oct. 29, 1996 to Kenneth B. Buell, et al); U.S. Pat. No. 6,120,487 (issued on Sep. 19, 2000 to Gregory Ashton); U.S. Pat. No. 6,120,489 (issued on Sep. 19, 2000 to Larry Johnson, et al); U.S. Pat. No. 4,940,464 (issued on Jul. 10, 1990 to Paul T. Van Gompel); U.S. Pat. No. 5,092,861 (issued on Mar. 3, 1992 to Hironori Nomura et al); U.S. Pat. No. 5,897,545 (issued on Apr. 27, 1999 to Mark James Kline, et al); U.S. Pat. No. 5,957,908 (issued on Sep. 28, 1999 to Mark James Kline, et al); and U.S. Patent Publication No. 2003/0233082 A1 (published on Dec. 18, 2003 to Mark J. Kline, et al).

Alternatively, the closed side interfaces 119a-b can be formed as disclosed in U.S. Pat. No. 5,779,831 (issued on Jul. 14, 1998 to Christoph Schmitz); U.S. Pat. No. 5,772,825 (issued on Jun. 30, 1998 to Christoph Schmitz); U.S. Pat. No. 5,607,537 (issued on Mar. 4, 1997 to Larry Johnson, et al); U.S. Pat. No. 5,622,589 (issued on Apr. 22, 2997 to Larry Johnson, et al); U.S. Pat. No. 5,662,638 (issued on Sep. 2, 1997 to Larry Johnson, et al); U.S. Pat. No. 6,042,673 (issued on Mar. 28, 2000 to Larry Johnson, et al); and U.S. Pat. No. 6,726,792 (issued on Apr. 27, 2004 to Larry Johnson, et al). The aforementioned patents disclose various processing methods to provide absorbent pull-on diapers. One of the processes utilizes a final knife followed by a reciprocating tucker blade that pushes the pad from a horizontal orientation to a vertical orientation and a vacuum conveyor belt that holds the pad through a high pressure side seaming unit. The side seaming unit is followed by a slitter that trims the pant edges to provide a finished seam edge. An alternative method disclosed in the aforementioned patents involves cutting the pad in the final knife and bi-folding the pad collecting the pads in a "waterwheel" stacker (a rotary slotted wheel). The bonding is accomplished while the pad is held in place on the rotating wheel.

Figure 7A:
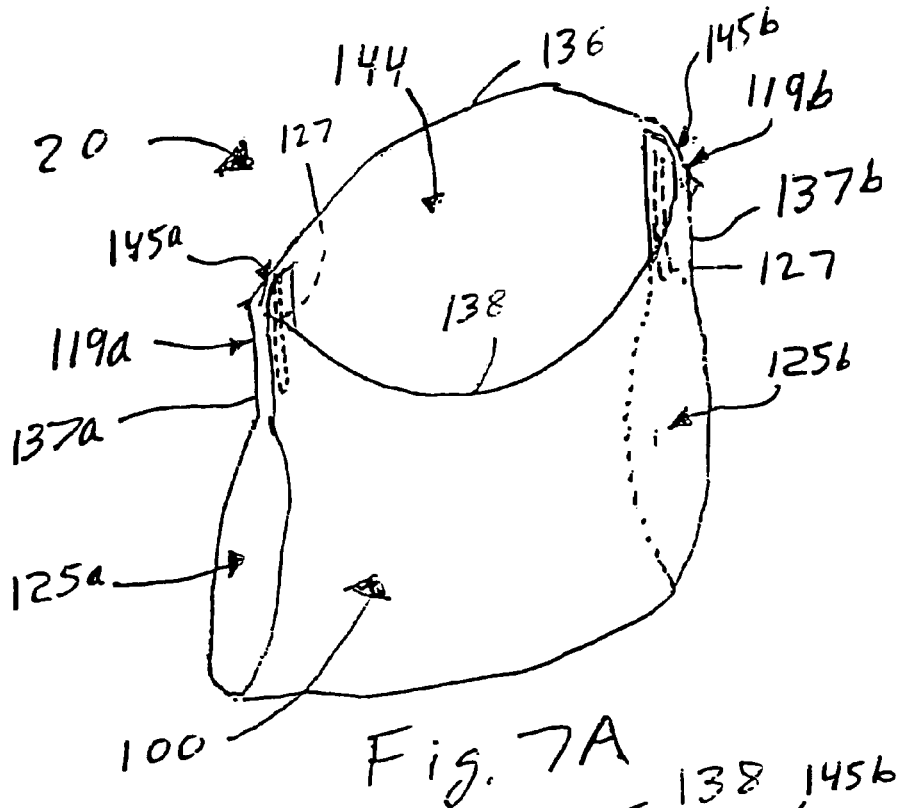
FIG. 7A is a schematic perspective view of the diaper illustrated in FIG. 1 configured as a pull-on diaper showing closed side interfaces constructed in accordance with one embodiment of the present invention.

Alternatively, referring to FIGS. 1 and 7A, a left side edge region 145a (defined as a region adjacent the left side edge 137a and including the left side edge 137a) at the front left attachment zone 143a (i.e., in the front waist region 36) is overlapped with the left side edge region 145a at the back attachment zone 150a (i.e., in the back waist region 38) in an interior surface-to-exterior surface (or vice versa) configuration. Likewise, a right side edge region 145b (defined as a region adjacent the right side edge 137b and including the right side edge 137b) at the front right attachment zone 143b (i.e., in the front waist region 36) is overlapped with the right side edge region 145b at the back attachment zone 150b (i.e., in the back waist region 38) in an interior surface-to-exterior surface (or vice versa) configuration. Accordingly, the left and right side interfaces 119a and 119b can be closed by attaching the overlapping attachment zones 143 and 150 via any suitable permanent or refastenable closure member 127, such as a seam of the type described above, or an adhesive, a cohesive, a tab-and-slot configuration, or via hook-and-loop attachments. It should be appreciated that joining the side edge regions 145a and 145b causes the side edges 137a and 137b to correspondingly be joined indirectly via the side edge regions 145a and 145b.

Figure 7B:
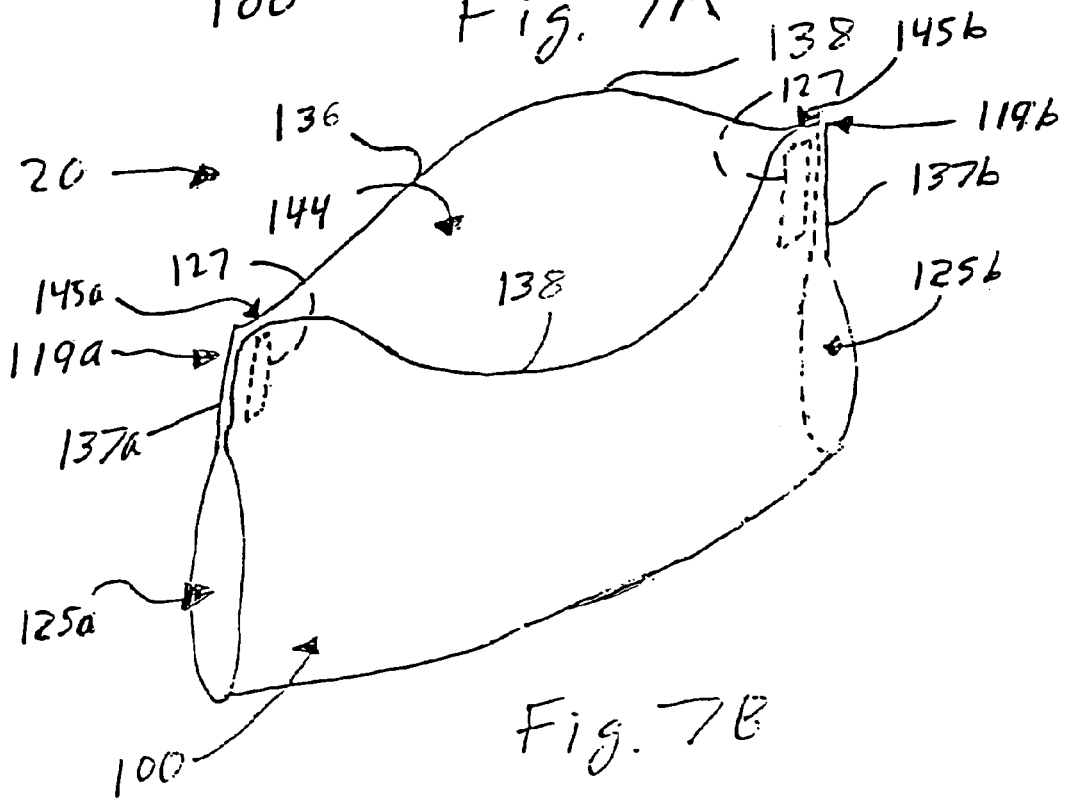
FIG. 7B is a schematic perspective view of the diaper illustrated in FIG. 1 configured as a pull-on diaper showing closed side interfaces constructed in accordance with an alternative embodiment.

Alternatively, referring to FIGS. 1 and 7B, the closed side interfaces 119a and 119b are formed by bi-folding the chassis 100 such that the left and right side edge regions 145a-b, adjacent the front waist edge 136, overlap the left and right side edge regions 145a-b, respectively, adjacent the back waist edge 138 in an interior-to-interior surface configuration. In this configuration, the front waist edge 136 can be substantially aligned with the back waist edge 138 and the side edge 137a in the front and back waist regions can also be substantially aligned as can be the front and back waist regions of side edge 137b. The folded chassis 100 is then attached at the side edge regions 145a-b at the attachment zones 143 and 150, respectively (FIG. 1), using any suitable permanent or refastenable closure member 127, thereby forming a pull-on diaper defining continuous left and right leg openings 125a and 125b, respectively, and a continuous, closed, waist opening 144.

Figure 7C:
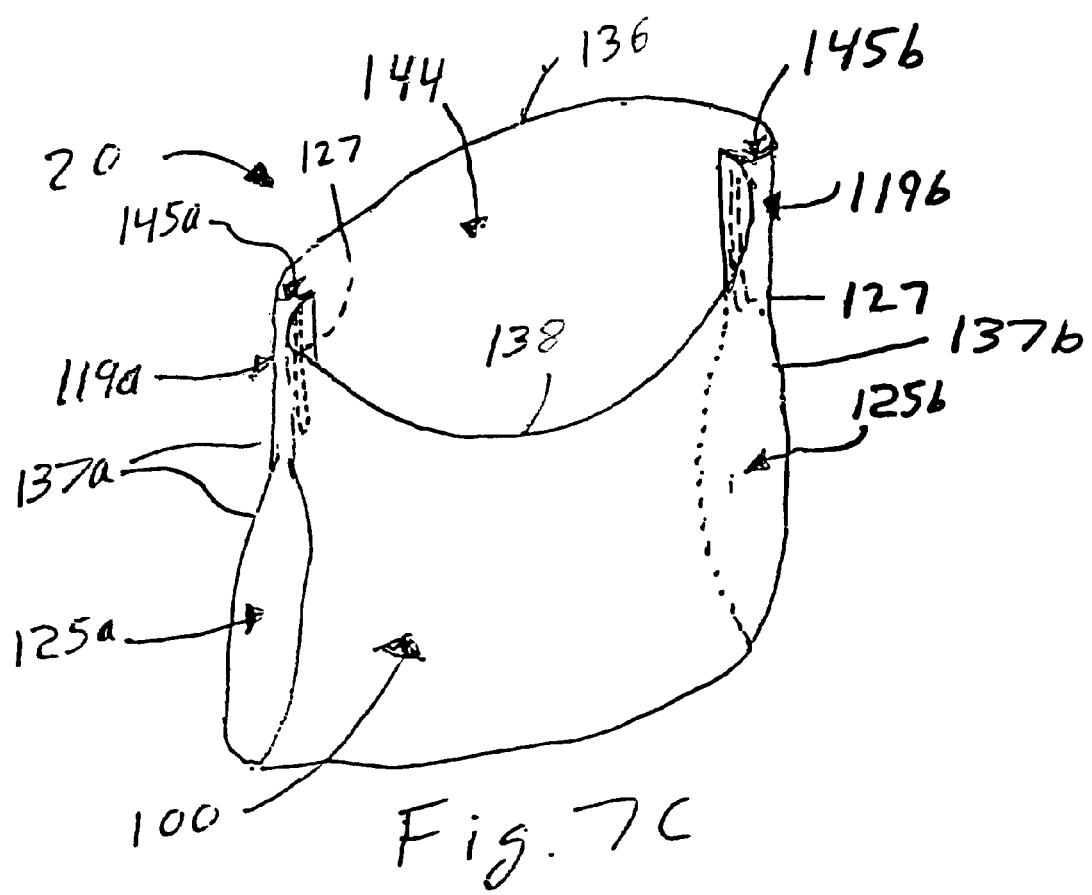
FIG. 7C is a schematic perspective view of the diaper illustrated in FIG. 1 configured as a pull-on diaper showing closed side interfaces constructed in accordance with an alternative embodiment.

Alternatively still, referring to FIGS. 1 and 7C, the closed side interfaces 119a and 119b can be formed by bi-folding chassis 100 such that the left and right side edge regions 145a-b, adjacent the front waist edge 136, overlap the left and right side edge regions 145a-b, respectively, adjacent the back waist edge 138 in an exterior-to-exterior surface configuration. In this configuration, the front end edge 136 can be substantially aligned with the back end edge 138. The folded chassis 100 is then attached at the side edge regions 145a-b at the attachment zones 143 and 150, respectively (FIG. 1), using any suitable permanent or refastenable closure member 127, thereby forming a pull-on diaper defining continuous left and right leg openings 125a and 125b, respectively, and a continuous, closed, waist opening 144.

Furthermore, one having ordinary skill in the art will appreciate that the side interfaces 119a-b can be closed via a refastenable closure member that can be nondestructively opened and refastened. Examples of refastenable closure members include hook-and-loop fasteners, snaps, tab-slot fasteners, cohesives, and the like.

Examples of closure members are described in U.S. Pat. No. 6,432,098 (issued Aug. 13, 2002 to Kline et al); U.S. Pat. No. 6,880,211 (issued Apr. 19, 2005 to Jackson et al); and U.S. Patent Publication No. 2003/0233082 (published Dec. 18, 2003 to Kline et al).

The present invention therefore recognizes that a plurality of pull-on diapers 20 can be pre-formed having the closed side interfaces 119a and 119b and packaged, and subsequently delivered to a user to prevent the need for the user (which could be the wearer) to close the side edges 137a and 137b prior to securing the diaper 20 on the wearer. Accordingly, referring to FIG. 9, the present invention includes the method of providing a plurality of pull-on diapers 20 of the type described above, placing the diapers 20 into a closed package or other containment apparatus 161 that retains the diapers 20. Accordingly, when the end user opens the packaging 161, the pull-on diaper can be donned on the wearer more easily than conventional taped diapers.

The term "pre-closed" refers to an absorbent article that can be closed by the end user and formed into a pant-like garment prior to applying the garment to the wearer. The term "pre-closed" also encompasses an absorbent article that has been formed into a pant-like garment in the packaging 161 such that the end user receives the article as a pant-like garment that can be directly applied to the wearer.

Description of the Chassis

Referring again to FIGS. 1-6, the chassis 100 includes a water-impermeable backsheet 26 that can be formed from any suitable material, such as a film of polyethylene or another polyolefin, or a film formed of coextruded polyolefin layers For example, a suitable coextruded film is available from Clopay Plastic Products Co. of Mason, Ohio, U.S.A. under the designation of M18-327. A multi-layer backsheet, such as a laminate of a film and a nonwoven or, alternatively, a dual layer nonwoven laminate, can also be suitable and can be oriented with the nonwoven disposed exteriorly to provide the feel and appearance of a cloth-like outermost layer, with the nonwoven disposed interiorly to separate the film from the skin of the wearer, or with nonwovens disposed both exteriorly and interiorly.

Part or all of the chassis 100 can be made extensible to a degree greater than the inherent extensibility of the material or materials from which the chassis 100 is made (e.g., the backsheet 26). Advantageously, the extensible chassis 100 can exhibit an elastic-like behavior in the direction of elongation without the use of added elastic materials. The elastic-like behavior can be modified and/or provided as desired in a web material 305 (FIG. 10) as described below. The additional extensibility may be desirable in order to allow the chassis 100 to conform to the body of a wearer during movement by the wearer. The additional extensibility may be desirable in order to allow the chassis 100 to conform to the body of a wearer during movement by the wearer. The additional extensibility may also be desirable, for example, to allow the user of a pull-on diaper 20 including a chassis 100 having a particular size before extension to extend the front and/or back waist regions 36 and 38 to enable the pull-on diaper to be pulled over the hips of the wearer and then to contract to encircle the waist of an individual wearer whose waist circumference is typically smaller than the circumference as measured at the hips of the wearer. Such extension of the waist region(s) can give the pull-on diaper 20 a generally hourglass shape, so long as the crotch region 37 is extended to a relatively lesser degree than the waist region(s), and can impart a tailored appearance to the pull-on diaper 20 when it is worn. In addition, the additional extensibility may be desirable in order to minimize the cost of the pull-on diaper 20. Specifically, a lesser amount of material is needed in order to make a diaper capable of being properly fit onto a given size of a wearer when the material is made extensible as described.

Additional extensibility in the chassis 100 in the lateral direction is relatively more useful than additional extensibility in the longitudinal direction. The abdomen of the wearer is likely to expand when the wearer changes posture from standing to sitting and the corresponding abdominal expansion increases the circumference that is encircled by the waist edges of the chassis 100, rendering lateral extension of the waist region or regions particularly advantageous.

Figure 10:
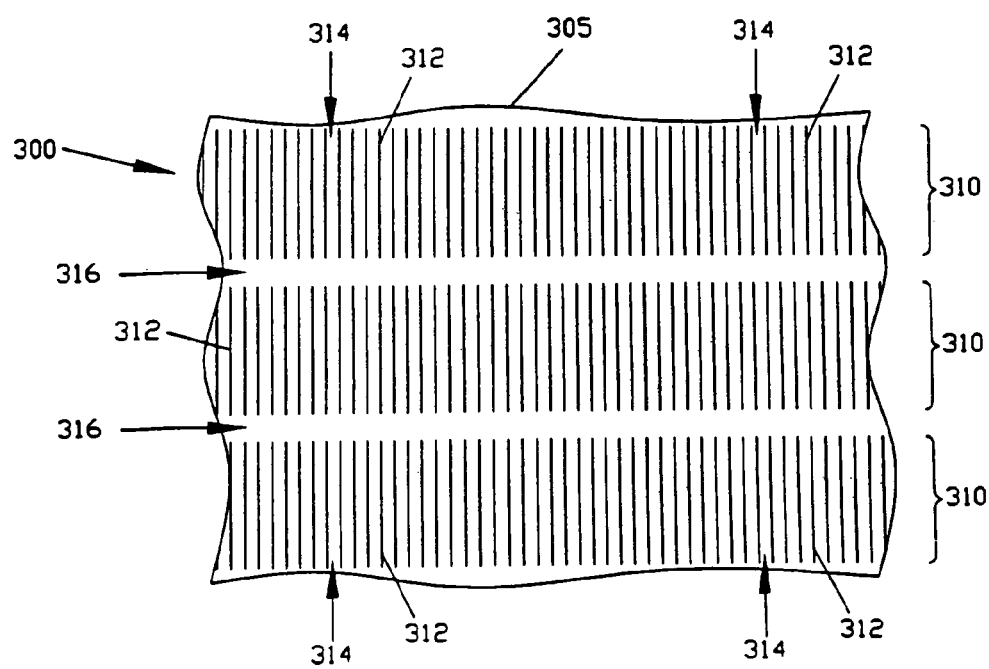
FIG. 10 is a plan view of an exemplary fragment of a formed web material.

Additional extensibility (e.g., lateral extensibility) in the chassis 100 can be provided in a variety of ways. For example, a material or materials from which the chassis 100 is made can be pleated by any of many known methods. Alternatively, all or a portion of the chassis 100 can be made of a formed elastic-like web material or a formed laminate of web materials like those described in U.S. Pat. No. 5,518,801 (issued on May 21, 1996 to Chappell et al.), U.S. Pat. No. 5,691,035 (issued Nov. 25, 1997 to Chappell et al), U.S. Pat. No. 5,723,087 (issued Mar. 3, 1998 to Chappell et al), U.S. Pat. No. 5,891,544 (issued Apr. 6, 1999 to Chappell et al), and U.S. Pat. No. 5,968,029 (issued Jan. 19, 1999 to Chappell et al). An exemplary fragment 300 of such a formed web material 305 is shown in FIG. 10. This formed web material 305 includes distinct laterally extending regions 310 in which the original material has been altered by embossing or another method of deformation to create a pattern of generally longitudinally oriented alternating ridges 312 and valleys 314. The formed web material 305 also includes laterally extending unaltered regions 316 located between the laterally extending altered regions 310.

Such a formed web material 305 can be laterally extended beyond its original dimension with the application of relatively less force than that required to extend the same material to the same extent when undeformed. In particular, the effects of an application of opposing divergent forces directed generally perpendicular to the ridges 312 and valleys 314 include an extension of such a formed web material along an axis between the opposing forces and generates a resistive contractive force, primarily in the unaltered regions 316. This resistive force is relatively smaller than the resistive force that is generated by the same material in its unaltered form when extended to the same extent, at least up to an extension at which the ridges and valleys in the altered regions flatten and begin to contribute to the resistive force. Thus, such formed web materials exhibit an extensible behavior resembling that of traditional elastic materials in the range of extensibility that is useful in absorbent articles, but may be made of relatively less expensive materials that are not inherently elastic and, thus, their use may provide an advantage in terms of the cost of manufacturing the absorbent articles. Such formed web materials can be made of relatively less expensive materials that are not inherently elastic and, thus, their use can provide an advantage in terms of the cost of manufacturing the absorbent articles.

When the web 325 is subjected to an applied elongation, the web material exhibits an elastic-like behavior as it extends in the direction of applied elongation and returns to its substantially untensioned condition once the applied elongation is removed, unless the web material is extended beyond the point of yielding. The web extensibility is adjustable by varying the percentage of the web surface which is comprised of the ridges 312 and valleys 314. This can be achieved, for instance, by modifying the widths of the ridges 312 and valleys 314, and the spacing between adjacent ridges 312 and valleys 314. A higher percentage of area coverage of the web material 325 by the ridges 312 and valleys will increase the overall extensibility of the web 325. The web 325 is able to undergo multiple cycles of applied elongation up to the yield point without losing its ability to substantially recover. Accordingly, the web 325 is able to return to its substantially untensioned condition once the applied elongation is removed (e.g., as the chassis 100 is pulled over the wearer's waist region during use).

In addition, different portions of the chassis 100 can be formed to have different ranges of extensibility and/or to be extensible to a greater or lesser degree when subjected to a given level of opposing tensile forces, i.e., to be relatively more easily or less easily extensible. Such differential extensibility can be desirable so that, for example, one or both of the waist regions 36 and 38 can be laterally extended relatively farther or relatively more easily than the crotch region 37.

Any of a variety of extensible materials can be formed as described in the Chappell et al. '801 patent. For example, a film, a nonwoven, or a laminate of either or both of these materials can be formed to provide the desired extensibility. It is also possible to modify such a material in more than one way while forming it to provide extensibility. For instance, a film that is originally formed to resist the permeation of vapor through its thickness and to contain fine particles of a granular filler material such as calcium carbonate can be treated as described in the Chappell et al. '801 patent to simultaneously provide extensibility and create small holes that allow water vapor to pass through its thickness. Thus, the film can simultaneously be rendered extensible and breathable. Alternatively, a portion of the backsheet 26 can be ring-rolled and thus rendered highly extensible as described in U.S. Pat. No. 5,366,782 (issued Nov. 22, 1994 to Curro, et al). Specifically, a ring-rolling apparatus includes opposing rolls having intermeshing teeth that incrementally stretch and thereby plastically deform the material forming backsheet 26 (or a portion thereof) thereby rendering the backsheet 26 extensible in the ring-rolled regions. In one embodiment, the backsheet 26 can be ring-rolled in a portion of at least one of the front or back waist regions while other regions may comprise a structured elastic-like formed web material. The chassis 100 can be ring-rolled across the entire width in one or both of the waist regions or alternatively can be ring-rolled over only a portion of the chassis width. In yet another embodiment the chassis 100 can be ring-rolled in the portion of the chassis 100 wherein the side flaps 147 overlap and are joined to the chassis 100 in attachment zones 151, 152, 153, and 154.

Furthermore, once the diaper 20 has been positioned on the lower torso region of the wearer, the web 325 enables the diaper 20 to apply a contractive force at the front and back waist regions 36 and 38, respectively, to the wearer's body at a level greater than 100 grams, alternatively greater than 200 grams, and alternatively still greater than 300 grams. It may also be desired that the chassis applies a contractive force at the waist regions 36 and 38 that is less than 2,000 grams, alternatively less than 1,500 grams and alternatively still less than 1,000 grams. As described in the Chappell et al. '801 patent, the resistive force exerted by the web 325 (i.e., the contractive force) in response to an applied elongation can be modified. Specifically, the web can be designed to yield virtually any resistive force which is less than that of the base web material by adjusting the percentage of the web surface which is comprised of the first and second regions. The higher the percent area coverage of the web 325 by the ridges 312 and valleys 314, the lower the resistive force that the web will exert against an applied elongation for a given material composition and cross-sectional area.

Extension versus force and contractive force can be determined by ASTM 882-02 with the following modifications. A sample representative of the extensible material disposed in the waist region should be collected for the test. In the test a 5.08 cm by 15.24 cm (2 inch by 6 inch) sample is cut from the material such that the edges are straight. The sample is clamped into the tensile tester. The clamps are attached 10.16 cm (4 in) from each other on the sample. The sample is pulled steadily at a speed of 2.54 cm/min (1 in/min) to 20% extension and then immediately returned to 0% (4 in. spacing between the clamps) at the same steady speed. Data, extension in mm and force in grams, should be collected at a rate of at least 1 data point per second. The data can be graphed to provide a curve of % extension versus force such that the extension at various tensile/contractive forces can be determined. The extension force can be determined by the extension curve and the contractive force can be determined by the return curve. This test should be repeated at 30, 40, 50, 60, 70, 80, 90 and 100% extension using a new specimen for each test. A representative sampling should be made for each condition.

To compare the extension force and contractive force of one pull-on diaper to another, the diaper in question is applied to a representative group of wearers within the specified size range of the diaper and the circumferential waist dimension of the diaper and/or wearer is determined. The circumferential waist dimension of the diaper as worn is then compared to the diaper waist circumference in a new unextended state. The % extension is derived by the following:

(As-worn waist circumference−original waist circumference)/original waist circumference Once the percentage waist extension is calculated, a correlating force can be established using the above-described method. It should thus be appreciated that, for a given diaper, a force-% extension relationship can be determined as described above.

Description of the Absorbent Assembly

As shown in FIGS. 1-6, the absorbent assembly 200 has left and right laterally opposing side flaps 247a and 247b. The side flaps are advantageously formed by folding portions of the absorbent assembly toward the longitudinal axis 42, to form both the respective side flaps 247a and 247b and the side edges 237a and 237b of the absorbent assembly 200. The side flaps 247a and 247b are water vapor-permeable, i.e., breathable, at least in the crotch region 37 where they form side barriers when the diaper is worn, as described in detail below.

Laterally opposing portions 107a and 107b of the chassis 100 in the crotch region 37 can be folded laterally inward to overlap the respective side flaps 247a and 247b and can be attached to the side flaps, for example, in the respective attachment zones 109a and 109b. Each of the folded laterally opposing portions 107a and 107b extends laterally only a part of the way from the respective side edge 237a or 237b of the absorbent assembly 200 toward the longitudinal axis 42, thus leaving uncovered respective exposed portions 207a and 207b of the side flaps.

In the exemplary diaper 20 shown in FIG. 1, the absorbent assembly 200 extends the full length of the chassis 100 between the front waist edge 136 and the back waist edge 138. Such a full length configuration may be desirable in order to minimize the amount of waste material and the difficulty associated with the manufacture of the diaper 20, especially when the method used to manufacture the diaper 20 requires the introduction of the material or materials for the absorbent assembly 200 in the form of a continuous web or multiple continuous webs. Also, such a full length configuration may be desirable in order to isolate the skin of the wearer from the backsheet. Alternatively, the absorbent assembly 200 can be shorter and extend less than the full length of the chassis 100. Such a shorter configuration may be desirable in order to minimize the total amount of material used and the cost of the diaper 20.

Each of the side flaps 247a and 247b is attached to the interior surface 202 of the absorbent assembly 200 in attachment zones located at or adjacent to the front edge 236 and the back edge 238. For example, in the absorbent assembly 200 shown in FIG. 1, the left side flap 247a is attached to the interior surface 202 of the absorbent assembly 200 in attachment zones 251a and 251c, while the right side flap 247b is attached to the interior surface 202 in attachment zones 251b and 251d. The attachment zones 251b and 251d can have equal areas or can be unequal in area. Between the attachment zones, the proximal edges 255a and 255b of the side flaps 247a and 247b remain free, i.e., are not attached to the interior surface 202 of the absorbent assembly 200.

Also between the attachment zones 251a and 251c, each side flap 247a and 247b can include a longitudinally extensible flap elastic member that is attached adjacent to the proximal edge of the corresponding side flap. For example, in the exemplary absorbent assembly 200 shown in FIG. 1, elastic strands 267a and 267b are attached adjacent to the respective proximal edge 255a and 255b of the side flaps 247a and 247b. The flap elastic member can be enclosed inside folded hems, such as the hems 271a and 271b shown in FIGS. 4-5. Alternatively, the flap elastic member can be sandwiched between two layers of the absorbent assembly 200 or can be attached on a surface of the absorbent assembly 200 and remain exposed.

When stretched, the flap elastic members allow the proximal edges of the side flaps to extend to the flat uncontracted length of the absorbent assembly, as shown in FIG. 1. When allowed to relax, the flap elastic members contract to gather the portions of the proximal edges along which the flap elastic members are attached. For example, when the exemplary diaper 20 is in a relaxed condition as shown in FIG. 11, the elastic strands 267a and 267b contract to gather the proximal edges 255a and 255b of the side flaps 247a and 247b. The contractive forces of the elastic strands 267a and 267b pull the front waist region 36 and the back waist region 38 toward each other and thereby bend the absorbent assembly 200 and the entire diaper 20 into a "U" shape in which the interior of the "U" shape is formed by the interior portions of the diaper. Because the proximal edges remain free between the attachment zones, the contractive forces of the elastic strands lift the proximal edges 255a and 255b and the exposed portions 207a and 207b of the side flaps away from the interior surface 202 of the absorbent assembly and thereby raise the breathable side flaps into position to serve as side barriers. The lateral spacing of the lifted proximal edges is selected to allow the deposit of bodily wastes from the lower torso of the wearer into the space between the raised side flaps 247a and 247b. The width of each of the side flaps 247a and 247b in effect becomes its height when the free portion of its proximal edge is lifted and the side flap is raised. This height can be selected to allow the lifted proximal edges 255a and 255b to fit into the leg creases of the body of the wearer to form seals to help prevent the leakage of deposited bodily waste out of the diaper.

Advantageously, the side flaps 247a and 247b provide side barrier protection from leakage from the core at the crotch region 37. Furthermore, it should be appreciated that the side flaps 247a and 247b are formed integrally with the absorbent assembly 200, as opposed to conventional absorbent articles which require discrete barrier protection elements to be fastened to the absorbent article. Accordingly, an absorbent article constructed in accordance with the principles of the present invention can be fabricated more efficiently, and thus less expensively, than conventional absorbent articles.

Figure 4:
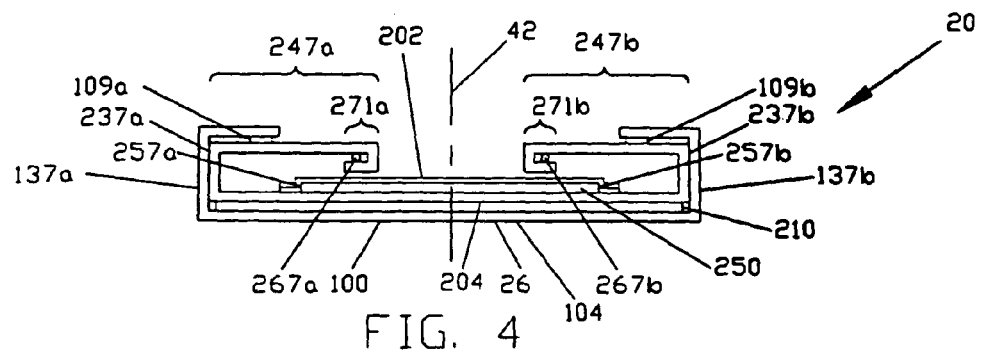
FIG. 4 is a sectional side elevation view of the diaper illustrated in FIG. 1 taken along line 4-4.
Figure 5:
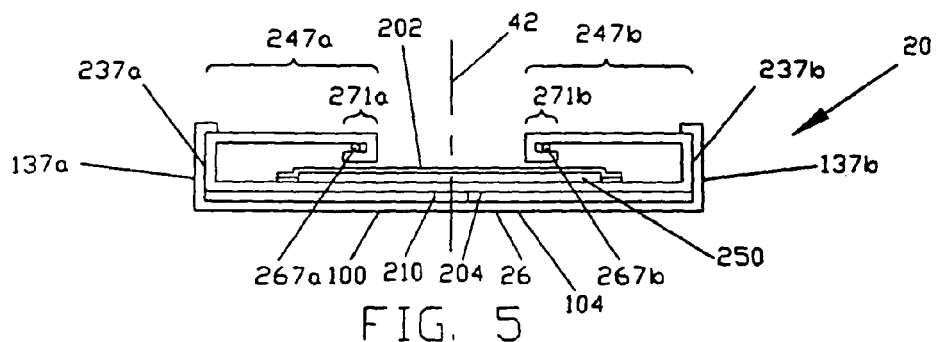
FIG. 5 is a sectional side elevation view of the diaper illustrated in FIG. 1 taken along 5-5.
Figure 6:
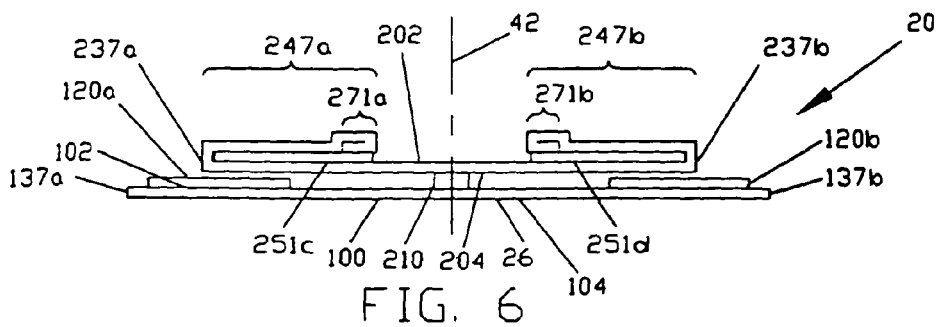
FIG. 6 is a sectional side elevation view of the diaper illustrated in FIG. 1 taken along line 6-6.
Figure 14:
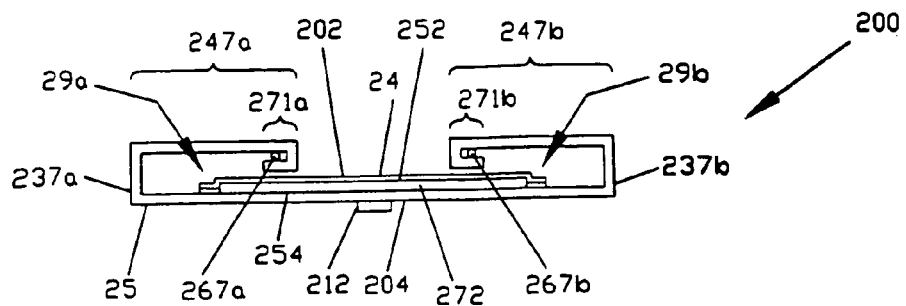
FIG. 14 is a section view of the absorbent assembly illustrated in FIG. 12 taken along line 14-14.

As shown in FIGS. 12-14, the absorbent assembly 200 includes an absorbent core 250 that serves to absorb and retain liquid bodily waste materials. The absorbent core 250 has a front edge 256, a back edge 258, a left side edge 257a, a right side edge 257b, an interior surface 252, and an exterior surface 254. As illustrated in FIGS. 4 and 5, the side flaps 247a and 247b can overlap the absorbent core 250, i.e., the proximal edges 255a and 255b of the side flaps can lie laterally inward of the respective left side edge 257a and right side edge 257b of the absorbent core 250. Alternatively, the side flaps 247a and 247b may not overlap the absorbent core.

Referring again to FIGS. 12-14, the absorbent assembly 200 can be attached to the 100 chassis over any part or the whole of the area of the absorbent assembly 200. In one aspect of the present invention, the absorbent assembly 200 is attached on its exterior surface 204 to the chassis 100, and in particular to the backsheet 26, in a cruciform attachment pattern, i.e., in an attachment pattern that forms or is arranged in a cross or "+" shape. The cruciform attachment pattern can be contiguous, i.e., all of its portions can be touching or connected throughout the pattern in an unbroken sequence. Alternatively, the cruciform attachment pattern can include detached portions and thereby lack contiguity but still be arranged such that the shape of the overall pattern is a cruciform. For example, a discontiguous cruciform attachment pattern can include a longitudinally extending portion disposed along the longitudinal axis and separate left and right laterally distal portions disposed along or adjacent to the lateral axis and thereby form a cruciform as the shape of the overall pattern An exemplary contiguous cruciform attachment pattern 210 is shown in FIGS. 2 and 12-14. When an adhesive is used for the attachment, less may be necessary in a cruciform attachment pattern than in a more extensive attachment pattern. In addition, the portions of the chassis that lie outside such a cruciform attachment pattern are not restrained by attachment to the absorbent assembly 200 and therefore remain extensible. In particular, a relatively narrow longitudinally extending portion 212 of a cruciform attachment pattern 210 like that shown in FIGS. 12 and 14 leaves the majority of the width of the chassis 100 in the front waist region 36 and in the back waist region 38 freely extensible and thereby allows extension of the chassis 100 in the lateral direction in these regions. A relatively wide laterally extending portion 214 of a cruciform attachment pattern 210 like that shown in FIGS. 12-13 prevents the portion of the chassis 100 in the crotch region 37 to which the absorbent assembly 200 is attached from shifting relative to the absorbent assembly 200 in that region and thereby contributes to the effectiveness of the raised side flaps. For example, if the chassis in the crotch region 37 were free to shift laterally such that the left side edge 137a and/or the right side edge 137b moved toward the longitudinal axis 42, the raised side flaps 247a and 247b might distort and fail to maintain contact with the body or become improperly positioned.

Within the extent of the cruciform attachment pattern 210, the absorbent assembly 200 can be attached to the chassis 100 continuously or intermittently. For example, a film of an adhesive can be applied continuously over the entire area of the cruciform attachment pattern and then used to continuously attach the absorbent assembly to the chassis 100. As an alternative example, an adhesive can be applied discontinuously at and inside the boundaries of the cruciform attachment pattern, such as in the form of dots, stripes, beads, spirals, etc., and then used to attach the absorbent assembly to the chassis 100.

The cruciform attachment pattern 210 can be disposed symmetrically with respect to either or both of the longitudinal axis 42 and the lateral axis 44 of the chassis 100. Alternatively, the cruciform attachment pattern 210 can be disposed asymmetrically with respect to either or both of the longitudinal axis 42 and the lateral axis 44. For example, the cruciform attachment pattern 210 shown in FIG. 21 is disposed symmetrically with respect to the longitudinal axis 42 and asymmetrically with respect to the lateral axis 44. In particular, the cruciform attachment pattern 210 shown in FIG. 21 is disposed asymmetrically toward the front waist region 36. Also, the laterally extending portion 214 of the cruciform attachment pattern 210 can be located distant from the lateral axis 44 and the longitudinally extending portion 212 of the cruciform attachment pattern 210 can similarly be located distant from the longitudinal axis 42. In addition, the cruciform attachment pattern 210 can be disposed symmetrically with respect to either or both of the side edges 237a and 237b and the front edge 236 and the back edge 238 of the absorbent assembly 200. For example, the cruciform attachment pattern 210 shown in FIG. 21 is disposed symmetrically with respect to both the side edges 237a and 237b and the front edge 236 and the back edge 238, i.e., the cruciform attachment pattern 210 shown in FIG. 21 is centered on the absorbent assembly 200. Alternatively, the cruciform attachment pattern 210 can be disposed asymmetrically with respect to either or both of the side edges 237a and 237b and front edge 236 and back edge 238 of the absorbent assembly 200, i.e., the cruciform attachment pattern 210 can be disposed off-center on the absorbent assembly 200.

It should be appreciated that the portion of the chassis 100 that is attached to the absorbent assembly 200 is not extensible. Advantageously, the cruciform attachment pattern 210 enables attachment of the absorbent assembly 200 to the chassis 100 while, at the same time, providing a significant portion of the chassis 100 that overlaps the absorbent assembly 200 to be free from the chassis 100, particularly in areas in the front waist region 36 and the back waist region 38. Accordingly, the cruciform attachment pattern 210 enables the chassis 100 to be more extensible than an absorbent article whose chassis is connected substantially to a surface of the absorbent assembly or about the periphery of the absorbent assembly. The increased chassis extensibility is useful when, for instance, donning the diaper 20 on the wearer.

Figure 17:
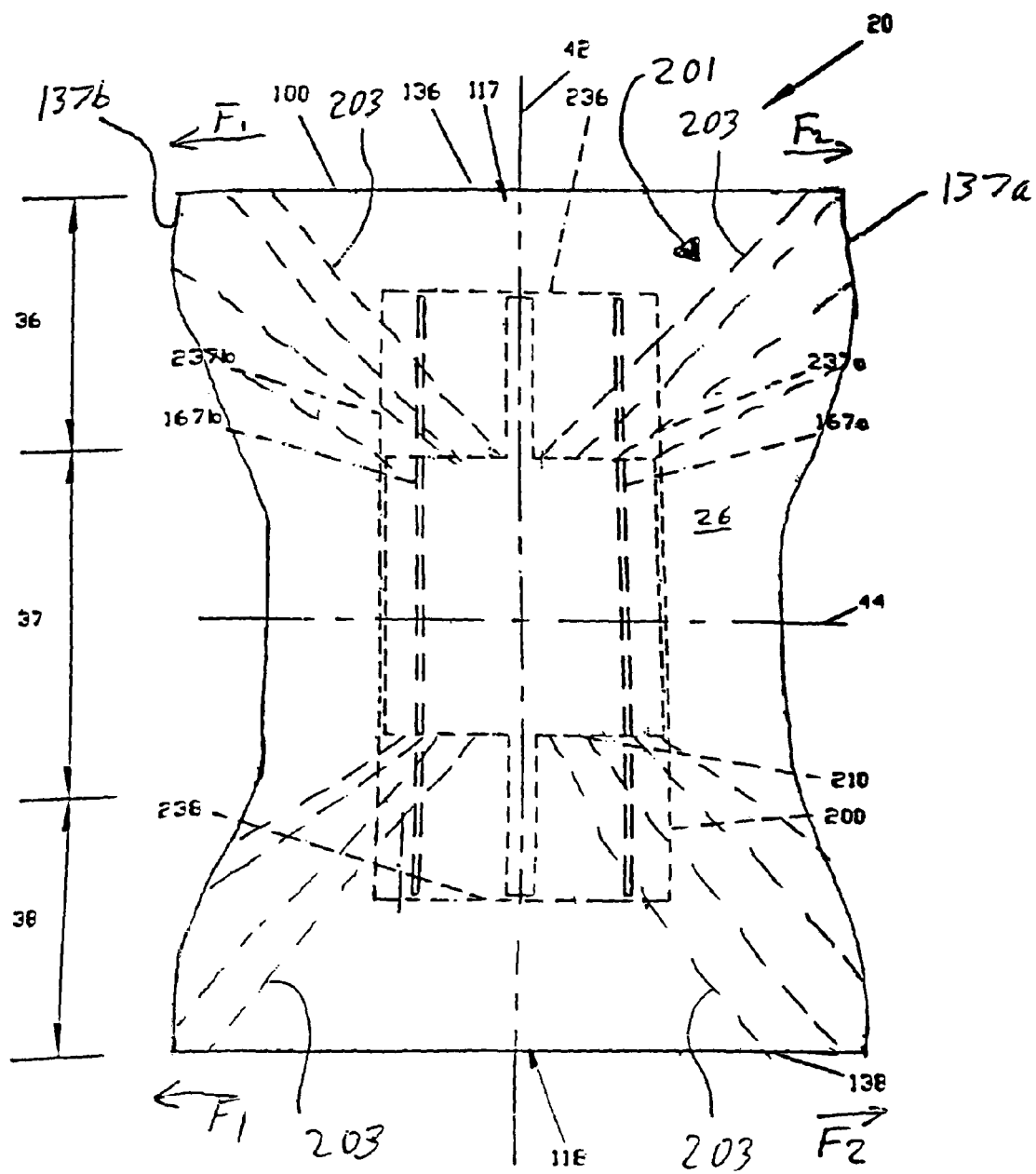
FIG. 17 is a plan view of an exemplary diaper having portions removed, wherein the diaper is shown in its flat, uncontracted state with forces applied to the diaper to simulate the diaper in a stretched configuration when worn about a lower torso region of a wearer.

Referring now to FIGS. 10 and 17, the backsheet 26, by virtue of the ridges 312 and valleys 314 described above, is extensible at regions that are free from the absorbent assembly 200, including regions that are disposed directly beneath the absorbent assembly 200 and free from the absorbent assembly 200. The extensibility of portions of the backsheet 26 increases as the portions become increasingly distant from the laterally extending portion 214 of the cruciform pattern 210.

When the pull-on diaper 20 is pulled onto the body of the wearer, a force will be applied by the diaper 20 to the waist region of the user to secure the diaper 20 onto the body of the wearer. Forces applied to the diaper 20 during application are simulated in FIG. 28 as opposing laterally outward forces F1 and F2 applied to the left and right side edges 137a and 137b, respectively, in the front waist region 36 and back waist region 38. Upon application of forces F1 and F2, the backsheet 26 deforms to a significantly greater degree in the waist region than in the crotch region thereby creating angled lines of tension 203 directed from portion 214 of the cruciform pattern 210 to the side edges 137a and 137b in both the front and back waist regions 36 and 38. These angled lines of tension 203 provide an internal support structure 201 integral with the chassis 100 (in particular the backsheet 26), that receives forces from the absorbent assembly 200 and transmits the forces toward the waist regions of the pull-on diaper, specifically toward the closed side interfaces.

Referring to FIGS. 12-14, the absorbent assembly 200 can include an upper covering sheet that is disposed in a face-to-face arrangement with the interior surface 252 of the absorbent core 250 and/or a lower covering sheet that is disposed in a face-to-face arrangement with the exterior surface 254 of the absorbent core 250 and the interior surface 102 of the chassis 100. If both are present, such an upper covering sheet and lower covering sheet can be attached together to contain the absorbent core 250 between them and thereby form the absorbent assembly 200. For example, in the exemplary absorbent assembly 200 shown in FIGS. 12-14, an upper covering sheet 24 and a lower covering sheet 25 are attached together at or adjacent to the side edges 237a and 237b of the absorbent assembly 200 in attachment zones 29a and 29b. Alternatively, the upper covering sheet 24 and the lower covering sheet 25 can be attached together in places other than the side edges 237a and 237b of the absorbent assembly 200, e.g., at or adjacent to the end edges 236 and 238 of the absorbent assembly 200, or at or adjacent to both the end edges 236 and 238 and the side edges 237a and 237b. Both the upper covering sheet 24 and the lower covering sheet 25 are water vapor-permeable, i.e., breathable.

The upper covering sheet 24 is water-permeable and allows liquid bodily waste to pass through its thickness to the absorbent core. The upper covering sheet 24 can be formed of a soft material that will not irritate the skin of the wearer, for example a synthetic nonwoven such as spunbonded or carded polypropylene, polyester, or rayon. The lower covering sheet 25 can be water-impermeable, and formed of any suitable material that is formed or treated to be breathable, for example the same material as the backsheet 26 (e.g., a polyolefinic film, a microporous breathable film, or a hydrophobic nonwoven).

The upper covering sheet 24 and the lower covering sheet 25 can extend to the same width and the same length. Alternatively, one or more of the edges of one of the covering sheets can lie distally relative to the respective edge or edges of the other covering sheet. For example, the upper covering sheet can extend longitudinally only to an extent sufficient to cover the absorbent core and to be attached to the lower covering sheet adjacent to either the front or the back edge of the absorbent core, while the lower covering sheet can extend longitudinally beyond the upper covering sheet toward or to the adjacent waist edge of the chassis. Such a longitudinally extended lower covering sheet can serve to isolate the skin of the wearer from a portion of the backsheet 26 as can be desirable, for example, when the diaper is worn under conditions in which contact between the skin and a backsheet film could be uncomfortable. Similarly, the upper covering sheet can extend laterally only to an extent sufficient to cover the absorbent core and to be attached to the lower covering sheet adjacent to either the left or the right side edge of the absorbent core and the lower covering sheet can extend laterally beyond the upper covering sheet. For example, in the exemplary absorbent assembly 200 shown in FIGS. 12-14, the upper covering sheet 24 extends laterally only a relatively small distance beyond the side edges 257a and 257b of the absorbent core 250 and is attached to the lower covering sheet 25 in this area. The lower covering sheet 25 in this exemplary absorbent assembly extends laterally beyond the upper covering sheet 24 and is folded to form the side flaps 247a and 247b.

The absorbent core 250 includes a storage component 272 that serves to absorb and retain liquid bodily waste materials. Suitable known materials can comprise any absorbent material that is generally compressible, conformable, non-irritating to the wearer's skin, and capable of absorbing and retaining liquids such as urine and other certain body exudates. The storage component 272 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. The storage component 272 can further comprise minor amounts (typically less than 10%) of non-liquid absorbent materials, such as adhesives, waxes, oils and the like. Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,209 (Dyer et al.); U.S. Pat. No. 5,397,316 (LaVon et al.); U.S. Pat. No. 5,625,222 (DesMarais et al.). These absorbent materials can be used separately or in combination. Many known absorbent materials can be used in a discrete form, i.e., in the form of fibers, granules, particles, and the like. Such a discrete form of an absorbent material can be immobilized by an adhesive that attaches the discrete pieces together to form a coherent layer or that attaches the discrete pieces to a substrate layer, or that attaches the discrete pieces both to each other and to the substrate layer. Alternatively, the core 250 can comprise an absorbent polymer material in contact with a thermoplastic material. The absorbent polymer material can be further mixed with an absorbent fibrous material, such as airfelt material, or absorbent core 250 can be substantially airfelt free, as described in U.S. patent application Ser. No. 10/776,851 (Becker et al), published as U.S. Publication. No. 2004/0162536.

The absorbent core 250 can include an acquisition component 290 in addition to one or more storage components. The absorbent core acquisition component 290 serves to acquire deposited liquid bodily waste material and transfer it to the absorbent core storage component. Any porous absorbent material which will imbibe and partition liquid bodily waste material to the storage component or components can be used to form the acquisition component. Suitable materials for the acquisition component 290 include synthetic fiber materials, open celled polymeric foam materials, fibrous nonwoven materials, cellulosic nonwoven materials, and various combination synthetic/cellulosic nonwoven materials. For example, the acquisition component can be formed of a nonwoven web or webs of synthetic fibers including polyester, polypropylene, and/or polyethylene, natural fibers including cotton and/or cellulose, blends of such fibers, or any equivalent materials or combinations of materials. Examples of such acquisition materials are more fully described in U.S. Pat. No. 4,950,264 issued to Osborn on Aug. 21, 1990. High loft nonwoven acquisition materials suitable for the acquisition component of the present invention can be obtained from Polymer Group, Inc., (PGI), 450 N.E. Blvd, Landisville, N.J. 08326, U.S.A., under the material code designation of 98920.

Such an absorbent core acquisition component 290 is shown overlying the absorbent core storage component 272 in FIGS. 12-14. A separation sheet 292 of, e.g., a tissue or a nonwoven material, can be disposed between the absorbent core storage component 272 and the absorbent core acquisition component 290 to help ensure that none of the gel formed by a superabsorbent polymer reaches the skin of the wearer. This separation sheet can extend laterally beyond the side edges of the absorbent core and the upper covering sheet can be attached to the separation sheet, which in turn can be attached to the lower covering sheet, rather than the upper covering sheet and the lower covering sheet being attached directly to each other. In this arrangement, the liquid bodily waste materials that is deposited onto the upper covering sheet 24 will pass through the thickness of the upper covering sheet 24 to be absorbed by the absorbent core acquisition component 290, and some or all of it can then pass through the thickness of the separation sheet 292 and then be absorbed and retained by the absorbent core storage component 272.

Figure 15:
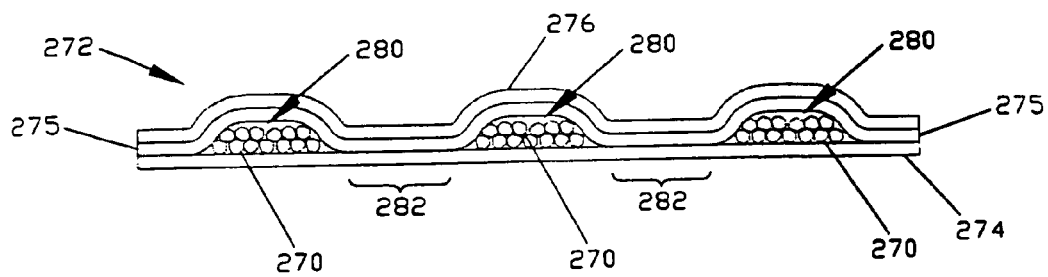
FIG. 15 is a sectional side elevation view of an exemplary absorbent assembly showing details of an exemplary absorbent core having particles of superabsorbent material contained inside pockets.

As shown in FIG. 15, in some exemplary embodiments, the absorbent core storage component 272 can include the discrete form of an absorbent material that is immobilized in pockets formed by a layer of a thermoplastic material, such as a hot melt adhesive, that intermittently contacts and adheres to a substrate sheet, while diverging away from the substrate sheet at the pockets. Absorbent core components having such structures and being suitable for the storage of liquid bodily wastes are described in co-pending and commonly assigned European Patent Applications Nos. 03 002 678.5 and 03 002 677.7, both filed on Feb. 12, 2003 in the name of Ehrnsperger et al., and in co-pending and commonly assigned U.S. patent applications Ser. Nos. 10/776,839 and 10/776,851, both filed on Feb. 11, 2004 in the name of Ehrnsperger et al. with respective priority claims to the aforementioned European Applications.

In the absorbent core storage component 272 illustrated in FIG. 15, particles 270 of a superabsorbent polymer are contained inside pockets 280 formed by a layer 275 of a thermoplastic material. The absorbent core storage component 272 can include both particles of a superabsorbent polymer and airfelt and both materials can be contained inside the pockets formed by the layer of the thermoplastic material. Alternatively, an exemplary absorbent core storage component may contain no airfelt and therefore the component can be made relatively thinner and more flexible for the comfort of the wearer. In addition, the particles of the superabsorbent polymer can be immobilized relatively more easily in the absence of airfelt. As shown in FIG. 15, the layer 275 of the thermoplastic material intermittently contacts and adheres to a substrate sheet 274 at the areas of attachment 282. Between the areas of attachment 282, the layer 275 diverges away from the substrate sheet 274 to form the pockets 280. The layer 275 can have the form of a sheet of fibers of the thermoplastic material through which the liquid bodily waste can pass to be absorbed by the particles 270 of the superabsorbent polymer.

In FIG. 15, a separate thermoplastic layer covering sheet 276 is shown overlying the layer 275 of the thermoplastic material. Alternatively, the separate thermoplastic layer covering sheet 276 can be omitted. As another alternative, two absorbent core storage components each like that shown in FIG. 15 except for the omission of the thermoplastic layer covering sheet 276 can be superposed with one absorbent core storage component inverted such that the respective substrate sheets distally oppose each other. In such a combination of absorbent core storage components, either or both of the distally opposing substrate sheets can serve respectively as either or both of an upper covering sheet and a lower covering sheet for the absorbent assembly. Alternatively, the absorbent assembly 200 can include a separate lower covering sheet that is disposed between the absorbent core and the interior surface of the chassis and/or a separate upper covering sheet that is disposed interiorly of the absorbent core.

Figure 16:
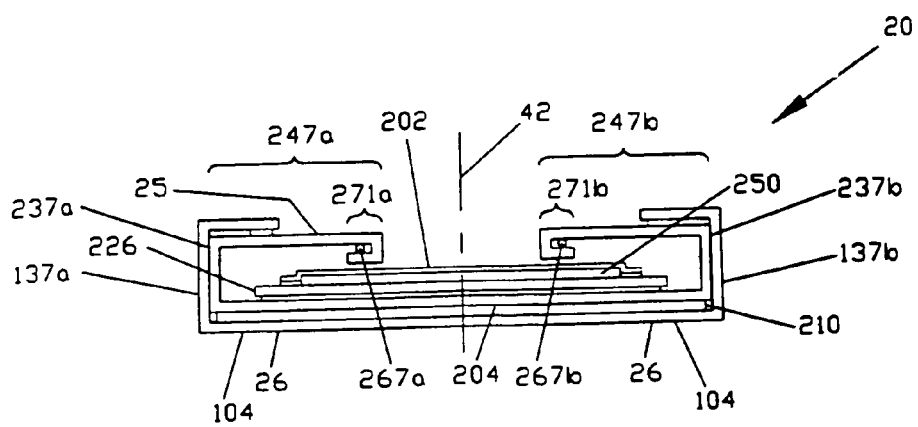
FIG. 16 is a sectional side elevation view of an exemplary absorbent assembly similar to FIG. 4, but including an additional bottom sheet.

The absorbent assembly 200 can include an additional bottom sheet of a film or other water-impermeable material to enhance the protection against leakage. For example, as shown in FIG. 16, an additional bottom sheet 226 of a film or other water-impermeable material can be attached inside the absorbent assembly 200 between the lower covering sheet 25 and the absorbent core 250. Alternatively, the bottom sheet 226 can be attached to the absorbent assembly exteriorly of the lower covering sheet. This bottom sheet 226 can extend laterally less far than either or both of the left side edge 237a and the right side edge 237b of the absorbent assembly 200, as shown in FIG. 16, or can extend laterally to overlap one or both of the side edges of the absorbent assembly.

The disclosures of all patents, patent applications and any patents which issue thereon, as well as any corresponding published foreign patent applications, and all publications listed and/or referenced in this description, are hereby incorporated herein by reference. It is expressly not admitted that any of the documents or any combination of the documents incorporated herein by reference teaches or discloses the present invention.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. An absorbent article comprising:
    a laterally elastically extensible chassis comprising a laterally continuous, water vapor-permeable backsheet, a front waist region, a back waist region, and a crotch region between the waist regions, laterally opposing side edges defining its width, longitudinally opposing front and back waist end edges defining its length, and an interior surface and an exterior surface, wherein the backsheet is the outermost layer of the absorbent article;
    an absorbent assembly comprising an absorbent core, upper covering sheet, lower covering sheet, and an interior and exterior surface, the absorbent assembly being attached to the interior surface of the chassis, and the absorbent core comprising its side edges and its end edges disposed proximally relative to the respective side edges and end edges of the chassis, wherein the upper covering sheet is the innermost layer of the absorbent article and wherein the lower covering sheet is intermediate of the upper covering sheet and the backsheet;
    wherein the lower covering sheet is folded laterally inward to form breathable side flaps, each side flap having a folded edge that is disposed laterally distal relative to a proximal edge of the side flap, and wherein a portion of the laterally continuous, water vapor-permeable backsheet in the crotch region is folded laterally inward and joined to at least a portion of laterally opposing breathable side flaps;
    wherein a portion of the laterally continuous, water vapor-permeable backsheet in at least one of the waist regions extends laterally outward beyond distal edges of the side flaps in the crotch region and is not joined to the laterally opposing breathable side flaps in the front and back waist regions;
    wherein the side flaps are attached to the interior surface of the absorbent assembly adjacent to their longitudinally distal ends in at least one of the front or back waist regions;
    wherein the chassis comprises first and second ear panels in the front waist region and third and fourth ear panels in the back waist region, each of the ear panels being integral with the chassis and formed at least in part by the laterally continuous, water vapor permeable backsheet; and
    wherein the first and second ear panels in the front waist region are joined to the third and fourth ear panels of the back waist region via closure members to form a waist opening and leg openings.

2. The absorbent article of claim 1 wherein a portion of the backsheet comprises at least two distinct laterally extending altered regions, each altered region containing a pattern of generally longitudinally oriented alternating ridges and valleys and also containing an unaltered region located between the altered regions.

3. The absorbent article of claim 1 wherein at least a portion of the chassis in one of the waist regions is laterally extensible to a maximum extensibility greater than a maximum extensibility of at least a portion of the chassis in the crotch region.

4. The absorbent article of claim 1 wherein at least a portion of the side flap is attached to the backsheet.

5. The absorbent article of claim 1 wherein the side flap comprises a proximal edge and when the absorbent article is in a flat and uncontracted state, is parallel to the side edges of the absorbent assembly.

6. The absorbent article of claim 1 further comprising an elastic gathering member, wherein the elastic gathering member, when the diaper is in a flat and uncontracted state, is parallel to the side edges of the absorbent assembly.

7. The absorbent article of claim 1 wherein the closure members are openable and refastenable.

8. The absorbent article of claim 7 wherein the closure members are cohesive fasteners.

9. The absorbent article of claim 7 wherein the closure members are mechanical fasteners.

10. The absorbent article of claim 1 wherein the backsheet comprises a film and a nonwoven.

11. The absorbent article of claim 1 wherein the absorbent assembly comprises a bottom sheet.

12. The absorbent article of claim 1 wherein the absorbent assembly is shorter in length (longitudinally) than the chassis.

13. The absorbent article of claim 1 wherein laterally opposing portions of the chassis in the crotch region are folded laterally inward to overlap the respective side flaps and are attached to the respective side flaps.

14. The absorbent article of claim 1 wherein the side flaps are water-vapor permeable.

15. The absorbent article of claim 1 wherein the lower covering sheet is water-vapor permeable.

16. The absorbent article of claim 1 wherein the absorbent assembly comprises a laterally continuous, water-impermeable, water vapor-permeable web that forms at least a portion of the lower covering sheet, wherein the laterally continuous layer forms at least a portion of the two laterally opposing breathable side flaps, and wherein the laterally continuous web forms at least a portion of two laterally opposing breathable hems.

17. The absorbent article of claim 16 herein each hem has a folded edge that is disposed laterally proximal relative to a distal edge of the hem.

\* \* \* \* \*